US012716888B2

(12) United States Patent
Lim et al.

(10) Patent No.: US 12,716,888 B2
(45) Date of Patent: Aug. 25, 2026

(54) COMPOSITION FOR DIAGNOSIS OR TREATMENT OF ANTICANCER DRUG RESISTANCE

(71) Applicant: Jong-Baeck Lim, Seoul (KR)

(72) Inventors: Jong-Baeck Lim, Seoul (KR); Jae-Il Choi, Seoul (KR); Hye Won Chung, Seoul (KR)

(73) Assignee: Jong-Baeck Lim, Seoul (KR)

( * ) Notice: Subject to any disclaimer, the term of this patent is extended or adjusted under 35 U.S.C. 154(b) by 885 days.

(21) Appl. No.: 17/905,491

(22) PCT Filed: Mar. 2, 2021

(86) PCT No.: PCT/KR2021/002550
§ 371 (c)(1),
(2) Date: Sep. 1, 2022

(87) PCT Pub. No.: WO2021/177691
PCT Pub. Date: Sep. 10, 2021

(65) Prior Publication Data

US 2024/0201168 A1 Jun. 20, 2024

(30) Foreign Application Priority Data

Mar. 2, 2020 (KR) ........................ 10-2020-0025872

(51) Int. Cl.

| | |
|---|---|
| ***C12N 15/113*** | (2010.01) |
| ***G01N 33/50*** | (2006.01) |
| ***G01N 33/68*** | (2006.01) |

(52) U.S. Cl.
CPC ........ *G01N 33/5011* (2013.01); *C12N 15/113* (2013.01); *G01N 33/5023* (2013.01); *G01N 33/6893* (2013.01); *C12N 2310/11* (2013.01); *G01N 2333/70585* (2013.01); *G01N 2800/44* (2013.01); *G01N 2800/52* (2013.01)

(58) Field of Classification Search
CPC ... A61P 35/00; C12N 15/113; C12N 2310/14; C12N 2310/11; C12N 15/1135; C12N 15/111
See application file for complete search history.

(56) References Cited

U.S. PATENT DOCUMENTS

| | | | |
|---|---|---|---|
| 2006/0122132 | A1 | 6/2006 | Touw |
| 2011/0105341 | A1 | 5/2011 | Semizarov |
| 2018/0200283 | A1 | 7/2018 | Moon |

FOREIGN PATENT DOCUMENTS

| | | | | |
|---|---|---|---|---|
| WO | WO-2009074968 | A2 * | 6/2009 | .......... C12Q 1/6886 |
| WO | 2014148429 | A1 | 9/2014 | |

OTHER PUBLICATIONS

Ueta et al., Influence of Citrobacter freundii on NINJ2 expression and oxaliplatin resistance in colorectal cancer, Cancer Medicine, vol. 14; e70940. pp. 1-14. (Year: 2025).*

Zhou et al., Ninjurin2 overexpression promotes glioma cell growth, Aging, 11(23) 11136-11147 (2019).

G. Li et al., "Ninjurin 2 overexpression promotes human colorectal cancer growth in vitro and in vivo," Aging, 11(19) 8526-41 (2019).

C. Holohan et al., "Cancer drug resistance: an evolving paradigm," Nat Rev Cancer, 13(10), 714-726 (2013).

G. Koehler and C. Milstein, "Derivation of specific antibody-producing tissue culture and tumor lines by cell fusion," Eur. J. Immunol., 6, 511-519 (1976).

T. Clackson et al., "Making antibody fragments using phage display libraries," Nature, 352, 624-628 (1991).

J.D. Marks et al., "By-passing Immunization: Human Antibodies from V-gene Libraries Displayed on Phage," J. Mol. Biol., 222, 581-597 (1991).

P.E. Nielsen et al., "Sequence-selective recognition of DNA by strand displacement with a thymine-substituted polyamide," Science 254, 1497-1500 (1991).

L.C. Bock et al., "Selection of single-stranded DNA molecules that bind and inhibit human thrombin," Nature, 355, 564-66 (1992).

F. Hoppe-Seyler and K. Butz, "Peptide aptamers: powerful new tools for molecular medicine," J. Mol. Med., 78(8), 426-30 (2000).

B.A. Cohen et al., "An artificial cell-cycle inhibitor isolated from a combinatorial library," Proc. Nat'l Acad. Sci. USA, 95 (24): 14272-77 (1998).

J. Weiler et al., "Anti-miRNA oligonucleotides (AMOs): ammunition to target miRNAs implicated in human disease?" Gene Therapy, 13, 496-502 (2006).

U. Nagai and K. Sato, "Synthesis of a bicyclic dipeptide with teh shape of beta-turn central part," Tetrahedron Lett., 26, 647-50 (1985).

Ewenson et al., "Ketomethylene Puedopeptide Analogues of Substance P: Synthesis and Biological Activity," J. Med. Chem., 29, 295-99 (1986).

A. Ewenson et al., "Synthesis, characterization and biological activity of keto methylene psuedopeptide analogs related to the C-terminal hexapeptide of Substance P," in Peptides: Structure and Function (Proceedings of the 9th American Peptide Symposium), Pierce Chemical Co., Rockland, IL, pp. 639-642 (1985).

K. A. Newlander et al., "Design and synthesis of novel disulfide mimetics," in Peptides: Chemistry and Biology, G.R. Marshall ed., EScOM Publisher: Leiden, Netherlands, pp. 763-765 (1988).

(Continued)

*Primary Examiner* — Dana H Shin
(74) *Attorney, Agent, or Firm* — McDonnell Boehnen Hulbert & Berghoff LLP

(57) ABSTRACT

The present invention relates to a composition for diagnosing resistance to a combination of ECF (Epirubicin, Cisplatin and 5-Fluorouracil; ECF), which is used for the treatment of gastric cancer, and a diagnostic kit comprising the same. In order to solve a problem that cancer recurrence and drug resistance occur due to an increase in tumor initiating cells (TICs) after treatment with a drug belonging to the ECF family, NINJ2 may be inhibited by early detection of resistance appearance, thereby suppressing the recurrence of gastric cancer and treating resistance to the drugs.

1 Claim, 15 Drawing Sheets

Specification includes a Sequence Listing.

(56) References Cited

OTHER PUBLICATIONS

V.M. Garsky et al., "Synthesis and characterization of tick anticoagulant mimetics," in Peptides: Chemistry and Biology, G.R. Marshall ed., EScOM Publisher: Leiden, Netherlands, pp. 908-910 (1988).
E.M. Gordon et al., "Design of Peptide Erived Amino Alcohols as Transition-State Analog Inhibitors of Angiotensin Converting Enzyme," Biochem Biophys Res Commun, 126, 419-426 (1985).
A.M. Nazdan et al., "Design of cholecystokinin analogs with high affinity and selectivity for brain CCK receptors," in Peptides: Chemistry and Biology, G.R. Marshall ed., EScOM Publisher: Leiden, Netherlands, pp. 100-102 (1988).
A.D. Ellington and J.W. Szostak, "In vitro selection of RNA molecules that bind specific ligands," Nature 346, 818-22 (1990).
International Search Report (with translation) and Written Opinion (with machine translation) in International Pat. App. PCT/KR2021/002550, dated Jul. 1, 2021.

* cited by examiner

Abs $IC_{50}$

ECF conc. (nM)

600
400
200
0
**
Parent
ECF-R
MKN-28/74

Abs $IC_{50}$

ECF conc. (nM)

1,500
1,000
500
0
**
Parent
ECF-R
MKN-74

Re-growth analysis of ECF-R cancer cells ns
**
**
Tamhane
Tumor weight [mg]
500
400
300
200
100
0
WT
siCtrl
siNINJ2
RES

| Drug response | N | NINJ2 Intensity | NINJ2 Extensive |
|---|---|---|---|
| PR, SD | 4 | 1.0±0.7 | 1.5±0.86 |
| PD | 7 | 1.57±0.36 | 3.0±0.0** |

SEQUENCE LISTING

```
<160> NUMBER OF SEQ ID NOS: 15

<210> SEQ ID NO 1
<211> LENGTH: 142
<212> TYPE: PRT
<213> ORGANISM: Homo sapiens

<400> SEQUENCE: 1

Met Glu Ser Ala Arg Glu Asn Ile Asp Leu Gln Pro Gly Ser Ser Asp
1               5                   10                  15

Pro Arg Ser Gln Pro Ile Asn Leu Asn His Tyr Ala Thr Lys Lys Ser
            20                  25                  30

Val Ala Glu Ser Met Leu Asp Val Ala Leu Phe Met Ser Asn Ala Met
        35                  40                  45

Arg Leu Lys Ala Val Leu Glu Gln Gly Pro Ser Ser His Tyr Tyr Thr
    50                  55                  60

Thr Leu Val Thr Leu Ile Ser Leu Ser Leu Leu Leu Gln Val Val Ile
65                  70                  75                  80

Gly Val Leu Leu Val Val Ile Ala Arg Leu Asn Leu Asn Glu Val Glu
                85                  90                  95

Lys Gln Trp Arg Leu Asn Gln Leu Asn Asn Ala Ala Thr Ile Leu Val
            100                 105                 110

Phe Phe Thr Val Val Ile Asn Val Phe Ile Thr Ala Phe Gly Ala His
        115                 120                 125

Lys Thr Gly Phe Leu Ala Ala Arg Ala Ser Arg Asn Pro Leu
    130                 135                 140


<210> SEQ ID NO 2
<211> LENGTH: 106
<212> TYPE: PRT
<213> ORGANISM: Homo sapiens

<400> SEQUENCE: 2

Met Leu Asp Val Ala Leu Phe Met Ser Asn Ala Met Arg Leu Lys Ala
1               5                   10                  15
```

```
Val Leu Glu Gln Gly Pro Ser Ser His Tyr Tyr Thr Thr Leu Val Thr
            20                  25                  30

Leu Ile Ser Leu Ser Leu Leu Leu Gln Val Val Ile Gly Val Leu Leu
        35                  40                  45

Val Val Ile Ala Arg Leu Asn Leu Asn Glu Val Glu Lys Gln Trp Arg
    50                  55                  60

Leu Asn Gln Leu Asn Asn Ala Ala Thr Ile Leu Val Phe Phe Thr Val
65                  70                  75                  80

Val Ile Asn Val Phe Ile Thr Ala Phe Gly Ala His Lys Thr Gly Phe
                85                  90                  95

Leu Ala Ala Arg Ala Ser Arg Asn Pro Leu
            100                 105


<210> SEQ ID NO 3
<211> LENGTH: 918
<212> TYPE: DNA
<213> ORGANISM: Homo sapiens

<400> SEQUENCE: 3

agagactcag acggcggagc ctggaggagc ccacgcagtc tgttcccggc acccggtgcg     60

tgtgaaggga cttgagggca gcgagatgga atcagcaaga gaaaacatcg accttcaacc    120

tggaagctcc gaccccagga gccagcccat caacctgaac cattacgcca ccaagaagag    180

cgtggcggag agcatgctgg acgtggccct gttcatgtcc aacgccatgc ggctgaaggc    240

ggtgctggag cagggaccat cctctcacta ctacaccacc ctggtcaccc tcatcagcct    300

ctctctgctc ctgcaggtgg tcatcggtgt cctgctcgtg gtcattgcac ggctgaacct    360

gaatgaggta gaaaagcagt ggcgactcaa ccagctcaac aacgcagcca ccatcttggt    420

cttcttcact gtggtcatca atgttttcat tacagccttc ggggcacata aaacagggtt    480

cctggctgcc agggcctcaa ggaatcctct ctgaatgcag cctgggaccc aggttctggg    540

cctggaactt ctgcctcctt cctccgtgat ctgccaggct cgtgggcact ttccacagcc    600

caggagagct tctgaaagga cagtatagct gcccttgctc cctacccaca gcacctgagt    660

taaaaagtga tttttatgtt attggtctaa gggacttcca tcttggtctg aagtcctgag    720

ctcagacgca ggtactgcca gccatacctt cctggtagca tctgctggac ctaagtaagg    780

catgtctgtc taaggccaag tctgcccggc ttaaggatgc tggttctgac tctaccccac    840

tgcttccttc tgctccaggc ctcaattttc ccttcttgta aaatggaatc tatatctata    900

aaggtttctt caaatcca                                                  918


<210> SEQ ID NO 4
<211> LENGTH: 926
<212> TYPE: DNA
<213> ORGANISM: Homo sapiens

<400> SEQUENCE: 4

gttgcaaagc agccgctcgg tggccgtaca acgcttcatc tctccgagcc tcggtttcct     60

catctccagc cctaaaatga cgacacgccc cacaggtctt gggaggatta agtgagggga    120

catgagcctg gaagctccga ccccaggagc cagcccatca acctgaacca ttacgccacc    180

aagaagagcg tggcggagag catgctggac gtggccctgt tcatgtccaa cgccatgcgg    240

ctgaaggcgg tgctggagca gggaccatcc tctcactact acaccaccct ggtcaccctc    300

atcagcctct ctctgctcct gcaggtggtc atcggtgtcc tgctcgtggt cattgcacgg    360

ctgaacctga atgaggtaga aaagcagtgg cgactcaacc agctcaacaa cgcagccacc    420
```

```
atcttggtct tcttcactgt ggtcatcaat gttttcatta cagccttcgg ggcacataaa    480

acagggttcc tggctgccag ggcctcaagg aatcctctct gaatgcagcc tgggacccag    540

gttctgggcc tggaacttct gcctccttcc tccgtgatct gccaggctcg tgggcacttt    600

ccacagccca ggagagcttc tgaaaggaca gtatagctgc ccttgctccc tacccacagc    660

acctgagtta aaaagtgatt tttatgttat tggtctaagg gacttccatc ttggtctgaa    720

gtcctgagct cagacgcagg tactgccagc catatccttcc tggtagcatc tgctggacct    780

aagtaaggca tgtctgtcta aggccaagtc tgcccggctt aaggatgctg gttctgactc    840

taccccactg cttccttctg ctccaggcct caattttccc ttcttgtaaa atggaatcta    900

tatctataaa ggtttcttca aatcca                                         926
```

```
<210> SEQ ID NO 5
<211> LENGTH: 21
<212> TYPE: DNA
<213> ORGANISM: Homo sapiens

<400> SEQUENCE: 5

cgtggtcatt gcacggctga a                                               21
```

```
<210> SEQ ID NO 6
<211> LENGTH: 21
<212> TYPE: DNA
<213> ORGANISM: Homo sapiens

<400> SEQUENCE: 6

ctgaacctga atgaggtaga a                                               21
```

```
<210> SEQ ID NO 7
<211> LENGTH: 779
<212> TYPE: PRT
<213> ORGANISM: Homo sapiens

<400> SEQUENCE: 7

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175
```

-continued

```
Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590
```

```
Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
        675                 680                 685

Glu Lys Glu Thr Arg Glu Glu Arg Ile Ile Thr Gly Pro Glu Ile Lys
    690                 695                 700

Tyr Thr Arg Ile Ser Thr Gly Gly Gly Glu Thr Glu Glu Thr Leu Lys
705                 710                 715                 720

Lys Leu Leu Gln Glu Glu Val Thr Lys Val Thr Lys Phe Ile Glu Gly
                725                 730                 735

Gly Asp Gly His Leu Phe Glu Asp Glu Glu Ile Lys Arg Leu Leu Gln
            740                 745                 750

Gly Asp Thr Pro Val Arg Lys Leu Gln Ala Asn Lys Lys Val Gln Gly
        755                 760                 765

Ser Arg Arg Arg Leu Arg Glu Gly Arg Ser Gln
    770                 775
```

<210> SEQ ID NO 8
<211> LENGTH: 340
<212> TYPE: PRT
<213> ORGANISM: Homo sapiens

<400> SEQUENCE: 8

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190
```

```
Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Arg His
    210                 215                 220

Ser His Gly Ser Gln Glu Gly Gly Ala Asn Thr Thr Ser Gly Pro Ile
225                 230                 235                 240

Arg Thr Pro Gln Ile Pro Glu Trp Leu Ile Ile Leu Ala Ser Leu Leu
                245                 250                 255

Ala Leu Ala Leu Ile Leu Ala Val Cys Ile Ala Val Asn Ser Arg Arg
            260                 265                 270

Arg Cys Gly Gln Lys Lys Lys Leu Val Ile Asn Ser Gly Asn Gly Ala
        275                 280                 285

Val Glu Asp Arg Lys Pro Ser Gly Leu Asn Gly Glu Ala Ser Lys Ser
    290                 295                 300

Gln Glu Met Val His Leu Val Asn Lys Glu Ser Ser Glu Thr Pro Asp
305                 310                 315                 320

Gln Phe Met Thr Ala Asp Glu Thr Arg Asn Leu Gln Asn Val Asp Met
                325                 330                 335

Lys Ile Gly Val
            340


<210> SEQ ID NO 9
<211> LENGTH: 58
<212> TYPE: DNA
<213> ORGANISM: Artificial Sequence
<220> FEATURE:
<223> OTHER INFORMATION: shNINJ2 Clone 1

<400> SEQUENCE: 9

ccggcgtggt cattgcacgg ctgaactcga gttcagccgt gcaatgacca cgtttttg       58


<210> SEQ ID NO 10
<211> LENGTH: 58
<212> TYPE: DNA
<213> ORGANISM: Artificial Sequence
<220> FEATURE:
<223> OTHER INFORMATION: shNINJ2 Clone 2

<400> SEQUENCE: 10

ccggctgaac ctgaatgagg tagaactcga gttctacctc attcaggttc agtttttg       58


<210> SEQ ID NO 11
<211> LENGTH: 23
<212> TYPE: RNA
<213> ORGANISM: Artificial Sequence
<220> FEATURE:
<223> OTHER INFORMATION: sense siNINJ2

<400> SEQUENCE: 11

guaaggcaug ucugucuaag gcc                                             23


<210> SEQ ID NO 12
<211> LENGTH: 23
<212> TYPE: RNA
<213> ORGANISM: Artificial Sequence
<220> FEATURE:
<223> OTHER INFORMATION: anti-sense siNINJ2

<400> SEQUENCE: 12

ggccuuagac agacaugccu uac                                             23
```

-continued

```
<210> SEQ ID NO 13
<211> LENGTH: 57
<212> TYPE: DNA
<213> ORGANISM: Artificial Sequence
<220> FEATURE:
<223> OTHER INFORMATION: control SHC002

<400> SEQUENCE: 13

ccggcaacaa gatgaagagc accaactcga gttggtgctc ttcatcttgt tgttttt        57


<210> SEQ ID NO 14
<211> LENGTH: 21
<212> TYPE: RNA
<213> ORGANISM: Artificial Sequence
<220> FEATURE:
<223> OTHER INFORMATION: sense control

<400> SEQUENCE: 14

uucuccgaac gugucacguu u                                               21


<210> SEQ ID NO 15
<211> LENGTH: 21
<212> TYPE: RNA
<213> ORGANISM: Artificial Sequence
<220> FEATURE:
<223> OTHER INFORMATION: anti-sense control

<400> SEQUENCE: 15

acgugacacg uucggagaau u                                               21
```

COMPOSITION FOR DIAGNOSIS OR TREATMENT OF ANTICANCER DRUG RESISTANCE

CROSS-REFERENCE TO RELATED APPLICATIONS

This application is a U.S. National Stage application of International Patent Application no. PCT/KR2021/002550, filed Mar. 2, 2021, which claims the benefit of priority of Korean Patent Application no. 10-2020-0025872, filed Mar. 2, 2020.

SEQUENCE LISTING

A computer readable form of the Sequence Listing is submitted via a USPTO patent electronic filing system. The Sequence Listing is contained in the sequence listing XML file created on Sep. 1, 2022, having the file name "22-1417-WO-US_SequenceListing_ST25.txt" and is 17 kb in size.

TECHNICAL FIELD

The present invention relates to a composition capable of diagnosing and treating anticancer drug resistance.

BACKGROUND

Cancer is one of the incurable diseases to be resolved by mankind, and huge capital has been invested in development to cure cancer worldwide. In Korea, cancer is the number one cause of death by disease, and more than 100,000 people are diagnosed with cancer annually, and more than 60,000 people die from cancer. In particular, gastric cancer is the fifth most frequently diagnosed disease in the world in 2018. Over the last decade, various anticancer therapies for cancer diagnosis and treatment have been developed rapidly, but the mortality rate due to cancer is still high. In addition, various anticancer drugs and attempts of various attempted anticancer therapies are still accompanied with side effects. Active studies have been conducted to reduce these side effects.

Pre-surgical chemotherapy or a combination of chemotherapy and radiotherapy for gastric cancer patients increases the survival rate compared to surgery alone. The 2017 version of the National Comprehensive Cancer Network (NCCN) guidelines proposed a combination therapy of three drugs (Epirubicin, Cisplatin and 5-Fluorouracil; ECF) as one of first-line chemotherapy regimens for gastric cancer, which was first developed by the Royal Marsden Hospital (England) in 1991. It has been confirmed that the 5-year survival rate of the group treated with the combination of ECF prior to surgery advantageously increases by about 15% or more compared to that of the group treated with surgery alone. Despite this advantage, drug resistance is a major factor that antagonizes the effectiveness of successful anticancer treatment, and worsens the prognosis of gastric cancer. Drug resistance (chemo-resistance) of cancer cells is divided into pre-existing resistance-mediating factors, and newly acquired drug resistance caused by drug administration (Cancer drug resistance: an evolving paradigm. Nat Rev Cancer. 2013 October; 13(10): 714-26.).

The causes of acquired drug resistance may include, for example, increased drug efflux, mutagenesis of drug targets, repair of DNA damage, activation of alternative signaling pathways, or avoidance of cell death induced by drug resistance. Even if a patient with drug resistance is treated with the drug, the effect of the treatment cannot be guaranteed, and thus there is a possibility that unnecessary time and cost burdens are imposed on the clinician and the patient. Therefore, when anticancer therapy is started, the therapy should be determined in consideration of the individual characteristics of the patient depending on the therapy. In addition, rather than blindly conducting the therapy, there is a realistic need for a criterion to estimate the therapy efficiency in advance through a specific biomarker so that a patient-tailored drug may be selectively used. As described above, there are few studies related to drug resistance, and thus the present inventors have discovered a marker that makes it possible to preselect patients resistant to ECF, thereby completing the present invention.

DETAILED DESCRIPTION

Technical Problem

Figure 1A:
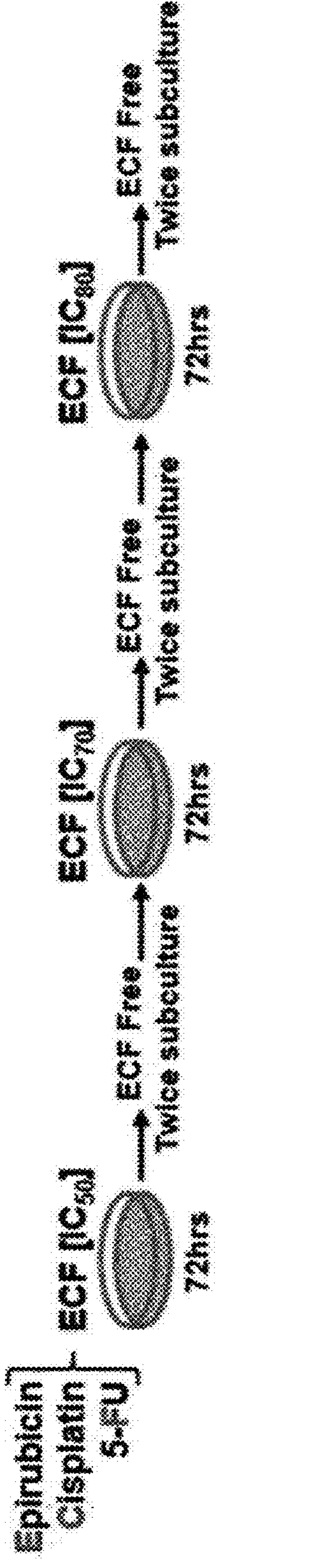
FIG. 1A shows a process of administering ECF drugs to each cell line according to one example of the present invention.

One object of the present invention is to provide a composition for diagnosing anticancer drug resistance.

Another object of the present invention is to provide a kit for diagnosing anticancer drug resistance.

Still another object of the present invention is to provide a method for providing information on anticancer drug resistance.

Yet another object of the present invention is to provide a pharmaceutical composition for preventing or treating cancer and a method for preventing or treating cancer.

Still yet another object of the present invention is to provide a pharmaceutical composition for treating anticancer drug resistance and a method for treating anticancer drug resistance.

A further object of the present invention is to provide a pharmaceutical composition for enhancing anticancer drug sensitivity and a method for enhancing anticancer drug sensitivity.

Another further object of the present invention is to provide a pharmaceutical composition for preventing or treating anticancer drug-resistant cancer and a method for preventing or treating anticancer drug-resistant cancer.

Still another further object of the present invention is to provide an anticancer drug-resistant cancer organoid.

Yet another further object of the present invention is to provide a method for screening either a drug for overcoming or treating anticancer drug resistance or a drug for enhancing anticancer drug sensitivity.

However, objects to be achieved by the present invention are not limited to the objects mentioned above, and other objects not mentioned herein will be clearly understood by those of ordinary skill in the art from the following description.

Technical Solution

Hereinafter, various embodiments described herein will be described with reference to the drawings. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order not to unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise defined in the specification, all the scientific and technical terms used in the specification have the same meanings as commonly understood by those skilled in the technical field to which the present invention pertains.

1. Use for Diagnosis of Anticancer Drug Resistance

One embodiment of the present invention is directed to a composition for diagnosing anticancer drug resistance.

In the present invention, the diagnostic composition may contain an agent for measuring the expression level of NINJ2 (nerve injury-induced protein 2; Ninjurin 2) protein or a gene encoding the same.

In the present invention, the protein encoded by the "NINJ2 (nerve injury-induced protein 2; Ninjurin 2)" gene belongs to the Ninjurin family that induces nerve damage. The NINJ2 protein refers to a cell surface adhesion protein that is upregulated in Schwann cells surrounding the distal segment of injured nerve and can play a role in nerve regeneration after nerve injury by promoting neurite outgrowth. Information on the NINJ2 protein and gene is available from the National Center for Biotechnology Information (NCBI) (Gene ID: 4815), and there are various variants of the NINJ2 protein or the gene encoding the same, including isoform-1, isoform-2, and isoform-3. The amino acid sequences of NINJ2 isoform 1 and isoform-3 used in the present invention are shown in SEQ ID NO: 1 and SEQ ID NO: 2, and the gene sequences encoding the NINJ2 isoform 1 and isoform 3 proteins are shown in SEQ ID NOs: 3 and 4. In the present invention, the NINJ2 protein or the gene encoding the same is of human origin, but the origin thereof is not limited to humans and may include any species.

In the present invention, the "NINJ2 protein or the gene encoding the same" may consist of the amino acid sequence of NINJ2 isoform 1 shown in SEQ ID NO: 1, the amino acid sequence of NINJ2 isoform 3 shown in SEQ ID NO: 2, the nucleotide sequence of NINJ2 isoform 1 shown in SEQ ID NO: 3, or the nucleotide sequence of NINJ2 isoform 3 shown in by SEQ ID NO: 4, without being limited thereto. Non-limiting examples thereof may include sequences having a homology of 99% to less than 100%, 95% to less than 99%, 90% to less than 95%, 85% to less than 90%, or 80% to less than 85% to the sequence of NINJ2, without being limited thereto, and may include all sequences as long as it is apparent to those skilled in the art that these sequences exert the desired effect of the present invention.

In the present invention, the term "drug" or "anticancer therapeutic drug" may be used interchangeably with the term "anticancer drug", and the term "anticancer drug" refers to a drug exhibiting an anticancer effect by killing cancer cells as well as cancer stem cells, and more preferably refers to a drug that is effective in treating gastric cancer.

In the present invention, the "anticancer drug" refers to a drug having a mechanism to kill cancer cells, and may be a drug comprising at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, and carmustine. Preferably, the anticancer drug may be a drug comprising at least one selected from the group consisting of epirubicin, cisplatin and 5-fluorouracil, and more preferably, may be a combination of ECF comprising epirubicin, cisplatin and 5-fluorouracil. In addition, the anticancer drug is not limited thereto and may comprise any drug belonging to the same family as ECF.

In the present invention, the "epirubicin" is a type of anticancer drug classified as a member of the anthracycline family, and is known to inhibit DNA and RNA synthesis by binding to DNA and inhibit cancer cells by inducing DNA cleavage through DNA topoisomerase 2. In addition, epirubicin can damage DNA by generating free radicals, and examples of drugs belonging to the same family as epirubicin include doxorubicin, daunorubicin, idarubicin, and the like.

In the present invention, the "cisplatin" is a type of anticancer drug classified as a member of the platinum family, and inhibits DNA repair and DNA synthesis through DNA crosslinking. Examples of anticancer drugs belonging to the platinum family include carboplatin, oxaliplatin, nedaplatin, triplatin tetranitrate, phenanthriplatin, satraplatin, picoplatin, and the like.

In the present invention, the "5-fluorouracil (5-FU)" is a type of anticancer drug classified as a member of the antimetabolite family, and is known to be used to inhibit cell division and tumor growth by inhibiting metabolites. Examples of anticancer drugs belonging to the antimetabolite family include 6-mercaptopurine (6-MP), capecitabine, cytarabine, floxuridine, fludarabine, gemcitabine, hydroxycarbamide, methotrexate, pemetrexed, phototrexate, and the like.

The "combination of ECF" in the present invention corresponds to a type of drug proposed as one of the first-line chemotherapy regimens for gastric cancer by the 2017 National Comprehensive Cancer Network (NCCN) guidelines. The combination of ECF is a drug first developed by the Royal Marsden Hospital (England) in 1991, and it is known that the 5-year survival rate of the group treated with the combination of ECF before surgery is increased. However, the combination of ECF poses problems in that cancer recurs due to an increase in tumor initiator cells (TIC) after treatment, and resistance to the ECF combination occurs. Therefore, studies on various mechanisms of action of the ECF combination are in progress.

In the present invention, anticancer drugs belonging to the same family as the ECF (epirubicin, cisplatin, and 5-fluorouracil) correspond to drugs that inhibit cancer cells by the same mechanism, and thus the results shown by ECF-resistant cells are not limited only to the results shown by the ECF combination, and are equally applicable to the results shown by any one or more anticancer drugs selected from the group consisting of the anthracycline family, the platinum family, and the antimetabolite family. Thus, drugs that act by the same mechanism are not limited to the above-mentioned drugs.

In the present invention, the term "anticancer drug resistance" means that the effect of an anticancer drug decreases when the anticancer drug is used quantitatively and repeatedly, and refers to a condition in which the frequency of use of an anticancer drug or the amount of anticancer drug used needs to be increased to obtain the same effect as previously experienced by the patient resistant to the anticancer drug, or a condition in which the same effect as before is not obtained even when the same dose of the anticancer drug as before is administered. In the present invention, a sample is diagnosed as having anticancer drug resistance, when a change in the expression level of the NINJ2 protein or the gene encoding the same increases compared to that of a normal control group.

In the present invention, the "diagnosing" is defined in a broad sense including: determining the susceptibility of a subject to an anticancer drug; determining whether or not the developed disease currently has anticancer drug resistance; determining the prognosis of anticancer drug-resistant cancer (e.g., determining responsiveness of cancer to the anticancer drug; or providing information about the diagnosis.

As used herein, the term "prognosis" refers to an action of predicting the course of a disease and the outcome of death or survival. The term "prognosis" or "diagnosis of prognosis" may be interpreted to mean any action of predicting the course of a disease before/after treatment by comprehensively considering the patient's disease course and condition which may vary depending on the patient's physiological or environmental condition. With regard to the purposes of the present invention, the term "prognosis" may be interpreted as either an action of predicting therapeutic responsiveness after treatment with an anticancer drug, preferably treatment with an anticancer drug which can be regarded as a drug belonging to the same family as each drug of ECF, more preferably treatment with the ECF combination, or an action of appropriately selecting whether or not to use the ECF combination, based on the result of predicting therapeutic responsiveness.

As used herein, the term "tumor" or "cancer" refers to a disease in which the cell cycle is not regulated and cells continues to divide, and is divided into carcinoma and sarcoma according to the site of occurrence. The term "carcinoma" refers to a malignant tumor that occurs in epithelial cells such as mucous cells or skin cells, and the term "sarcoma" refers to a malignant tumor that occurs in non-epithelial cells such as muscle, connective tissue, bone, cartilage, or blood vessel cells.

In the present invention, anticancer treatment of the cancer patient may be performed using one or more selected from the group consisting of epirubicin, cisplatin and 5-fluorouracil, more preferably a combination of ECF (epirubicin, cisplatin and 5-fluorouracil) comprising epirubicin, cisplatin and 5-fluorouracil. In addition, any anticancer drug that may be regarded as a drug belonging to the same family as each of ECF may be used without limitation.

In the present invention, prediction of the prognosis may be prediction of therapeutic responsiveness after treatment of a cancer patient with the anticancer agent, and may be prediction of whether resistance to the anticancer drug occurs.

As used herein, the term "cancer" as a disease to be treated refers to or describes the physiological condition in mammals that is typically characterized by unregulated cell growth. The cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, CNS central nervous system tumor, primary CNS lymphoma, spinal cord tumor, brainstem glioma, or pituitary adenoma. However, the cancer is not limited thereto and may be any type of cancer in which cancer progression, such as tumor differentiation and/or proliferation, is dependent on cancer cells and/or cancer stem cells as described in the present invention.

The composition for diagnosing anticancer drug resistance according to the present invention may further contain an agent for measuring the expression level of either at least one of periostin and CD44 proteins, or a gene encoding at least one protein.

As used herein, the term "periostin" is also called POSTN, PN, or osteoblast-specific factor OSF-2 and refers to a protein encoded by the POSTN gene in humans. In addition, the periostin protein is known to act as a ligand for alpha-V/beta-3 and alpha-V/beta-5 integrins to enable epithelial cell adhesion and migration. The periostin protein is a Gla domain vitamin K-dependent factor, and is also known to increase cell survival, invasion, angiogenesis, metastasis and epithelial-mesenchymal transition by activating Akt/PKB and FAK-mediated signaling pathways through binding to integrins of cancer cells in many cancers.

In the present invention, information on the periostin protein and gene is available from the National Center for Biotechnology Information (NCBI) (Gene ID: 10631), and the amino acid sequence of periostin used in the present invention is shown in SEQ ID NO: 7. In the present invention, the periostin protein or the gene encoding the same is of human origin, but the origin thereof is not limited to humans and may include any species. Non-limiting examples thereof may include sequences having a homology of 99% to less than 100%, 95% to less than 99%, 90% to less than 95%, 85% to less than 90%, or 80% to less than 85% to the sequence of periostin, without being limited thereto, and may include all sequences as long as it is apparent to those skilled in the art that these sequences exert the desired effect of the present invention.

As used herein, the term "CD44" refers to a marker expressed in the plasma membrane of cells or cancer stem cells such as drug-resistant cancer cells. More specifically, CD44 antigen refers to a cell surface glycoprotein that is involved in cell-cell interaction, cell adhesion and migration. CD44 is known to play a key role in tumorigenesis, and plasticity and chemical resistance of cancer stem cells.

In the present invention, information on the CD44 protein and gene is available from the National Center for Biotechnology Information (NCBI) (Gene ID: 960), and the amino acid sequence of CD44 used in the present invention is shown in SEQ ID NO: 8. In the present invention, the CD44 protein or the gene encoding the same is of human origin, but the origin thereof is not limited to humans and may include any species. Non-limiting examples thereof may include sequences having a homology of 99% to less than 100%, 95% to less than 99%, 90% to less than 95%, 85% to less than 90%, or 80% to less than 85% to the sequence of CD44, without being limited thereto, and may include all sequences as long as it is apparent to those skilled in the art that these sequences exert the desired effect of the present invention.

In the composition for diagnosing anticancer drug resistance according to the present invention, the agent for measuring the expression level of the protein may comprise at least one selected from the group consisting of an antibody, an oligopeptide, a ligand, a peptide nucleic acid (PNA) and an aptamer, which bind specifically to the protein, without being limited thereto.

As used herein, the "antibody" refers to a substance that binds specifically to an antigen, causing an antigen-antibody reaction. With regard to the purposes of the present invention, the antibody refers to an antibody that binds specifically to the protein. The antibodies of the present invention include all polyclonal antibodies, monoclonal antibodies, and recombinant antibodies. The antibody may be easily produced using techniques well known in the art. For example, the polyclonal antibody may be produced by a method well known in the art, which comprises a process of injecting the protein antigen into an animal, collecting blood from the animal, and isolating serum containing the antibody. This polyclonal antibody may be produced from any animal species such as goats, rabbits, sheep, monkeys, horses, pigs, cattle, or dogs. In addition, the monoclonal antibody may be produced using a hybridoma method (see Kohler and Milstein (1976), European Journal of Immunology, 6:511-519) well known in the art, or phage antibody library technology (see Clackson et al., Nature, 352:624-628, 1991; Marks et al., J. Mol. Biol., 222:58, 1-597, 1991). The antibody produced by the above method may be isolated and purified using methods such as gel electrophoresis, dialysis, salt precipitation, ion exchange chromatography, and affinity chromatography. In addition, the antibodies of the present invention include functional fragments of antibody molecules as well as complete forms having two full-length light chains and two full-length heavy chains. The expression "functional fragments of antibody molecules" refers to fragments retaining at least an antigen-binding function, and examples of the functional fragments include Fab, F(ab'), F(ab')2, and Fv.

In the present invention, the "oligopeptide" is a peptide consisting of 2 to 20 amino acids, and examples thereof include, but are not limited to, a dipeptide, a tripeptide, a tetrapeptide, and a pentapeptide.

In the present invention, the "peptide nucleic acid (PNA)" refers to an artificially synthesized polymer similar to DNA or RNA, and was first introduced by professors Nielsen, Egholm, Berg and Buchardt (at the University of Copenhagen, Denmark) in 1991. DNA has a phosphate-ribose backbone, whereas PNA has a backbone composed of repeating units of N-(2-aminoethyl)-glycine linked by peptide bonds. Thanks to this structure, PNA has a significantly increased binding affinity for DNA or RNA and a significantly increased stability, and thus is used in molecular biology, diagnostic analysis, and antisense therapy. PNA is disclosed in detail in Nielsen P E, Egholm M, Berg R H, Buchardt O (December 1991), "Sequence-selective recognition of DNA by strand displacement with a thymine-substituted polyamide", Science 254 (5037): 1497-1500.

In the present invention, the "aptamer" is an oligonucleic acid or peptide molecule, and general contents of the aptamer are disclosed in detail in Bock L C et al., Nature 355(6360): 564-6(1992); Hoppe-Seyler F, Butz K "Peptide aptamers: powerful new tools for molecular medicine". J Mol Med. 78(8): 42630(2000); Cohen B A, Colas P, Brent R. "An artificial cell-cycle inhibitor isolated from a combinatorial library". Proc Natl Acad Sci USA. 95(24): 142727 (1998).

In the composition for diagnosing anticancer drug resistance according to the present invention, the agent for measuring the expression level of the gene encoding the protein may comprise at least one selected from the group consisting of a primer, a probe and an antisense nucleotide, which bind specifically to the gene encoding the protein, without being limited thereto.

In the present invention, the "primer" is a fragment that recognizes a target gene sequence, and includes a pair of forward and reverse primers. Preferably, the primer is a primer pair that provides analysis results with specificity and sensitivity. Because the nucleotide sequence of the primer does not match a non-targeted sequence in a sample, the primer can show high specificity when it amplifies only a target gene sequence containing a complementary primer binding site without causing non-specific amplification.

In the present invention, the "probe" refers to a substance which is capable of binding specifically to the target substance to be detected in a sample and may specifically identify the presence of the target substance in the sample through the binding. The kind of the probe is not specifically limited, as long as it is a substance that is generally used in the art. Preferably, the probe may be peptide nucleic acid (PNA), locked nucleic acid (LNA), a peptide, a polypeptide, a protein, RNA or DNA. Most preferably, the probe is PNA. More specifically, the probe may be a biomaterial derived from an organism, an analogue thereof, or a material produced ex vivo, and examples thereof include enzymes, proteins, antibodies, microorganisms, animal/plant cells and organs, neural cells, DNA, and RNA. Examples of the DNA include cDNA, genomic DNA, and oligonucleotides, examples of the RNA include genomic RNA, mRNA, and oligonucleotides, and examples of the protein include antibodies, antigens, enzymes, and peptides.

In the present invention, the "locked nucleic acid (LNA)" refers to a nucleic acid analog containing a 2'-O or 4'-C methylene bridge [J Weiler, J Hunziker and J Hall Gene Therapy (2006) 13, 496.502]. LNA nucleosides include common nucleic acid bases of DNA and RNA, and can form base pairs according to the Watson-Crick base pairing rule. However, due to 'locking' of the molecule attributable to the methylene bridge, the LNA fails to form an ideal shape in the Watson-Crick bond. When the LNA is incorporated in a DNA or RNA oligonucleotide, it can more rapidly pair with a complementary nucleotide chain, thus increasing the stability of the double strand.

In the present invention, the "antisense" refers to an oligomer having a sequence of nucleotide bases and a subunit-to-subunit backbone that allows the antisense oligomer to hybridize to a target sequence in an RNA by Watson-Crick base pairing, to form an RNA: oligomer heteroduplex within the target sequence, typically with an mRNA. The oligomer may have exact sequence complementarity to the target sequence or near complementarity.

Information on the NINJ2, periostin or CD44 protein according to the present invention or on the genes encoding the same is known. Thus, based on this information, those skilled in the art can easily design a primer, a probe or an antisense nucleotide, which specifically binds to the gene encoding the protein.

Another embodiment of the present invention is directed to a kit for diagnosing anticancer drug resistance comprising the composition for diagnosing anticancer drug resistance according to the present invention.

In the present invention, the "kit" refers to a tool capable of evaluating the expression level of a biomarker by labeling a probe or antibody, which specifically binds to a biomarker component, with a detectable label. The term "labeling", with regard to the probe or antibody, is intended to encompass direct labeling of the probe or antibody by coupling a detectable substance to the probe or antibody, as well as indirect labeling of the probe or antibody by reactivity with another reagent that is directly labeled. The kit may comprise a chromogenic substrate solution to induce the chromogenic reaction with the label; a washing solution; and other solutions, and may be prepared to comprise reagent components to be used. In the present invention, the kit may be a kit comprising essential elements necessary for performing RT-PCR, and may comprise, in addition to each primer pair specific for a marker gene, a test tube, reaction buffer, deoxynucleotides (dNTPs), Taq-polymerase, reverse transcriptase, DNase, RNase inhibitors, sterile water, and the like. In addition, the kit may be a kit for detecting a gene for predicting HPD prognosis, which comprises essential elements necessary for performing DNA chip assay. The DNA chip kit may comprise a substrate to which cDNA corresponding to a gene or a fragment thereof is attached as a probe, and the substrate may include cDNA corresponding to a quantitative control gene or a fragment thereof. The kit of the present invention is not limited thereto and may be any kit known in the art.

In the present invention, the kit may be, but is not limited to, an RT-PCR kit, a DNA chip kit, an ELISA kit, a protein chip kit, a rapid kit or a multiple-reaction monitoring (MRM) kit.

The kit of the present invention may further comprise one or more other component compositions, solutions or devices suitable for analysis methods. For example, the kit according to the present invention may further comprise essential elements necessary for performing reverse transcription polymerase reaction. The reverse transcription polymerase reaction kit comprises a pair of primers specific to a gene encoding a marker protein. Each primer is a nucleotide having a sequence specific to the nucleic acid sequence of the gene, and may have a length of about 7 bp to 50 bp, more preferably about 10 bp to 30 bp. In addition, the kit may comprise primers specific to the nucleic acid sequence of a control gene. In addition, the reverse transcription polymerase reaction kit may comprise a test tube or other suitable container, buffers (having various pHs and magnesium concentrations), deoxynucleotides (dNTPs), enzymes such as Taq-polymerase and reverse transcriptase, DNAse and RNAse inhibitors, DEPC-water, sterile water, and the like.

In addition, the kit for diagnosing anticancer drug resistance according to the present invention may comprise essential elements necessary for performing DNA chip assay. The DNA chip kit may comprise a substrate to which a gene or a cDNA or oligonucleotide corresponding to a fragment thereof is attached, and reagents, agents, and enzymes for constructing a fluorescently labeled probe. In addition, the substrate may comprise a control gene or a cDNA or oligonucleotide corresponding to a fragment thereof.

In addition, the kit for diagnosing anticancer drug resistance according to the present invention may comprise essential elements necessary for performing ELISA. The ELISA kit may comprise an antibody specific to the protein. The antibody has high specificity and affinity for the marker protein, with no cross-reactivity to other proteins, and may be a monoclonal antibody, a polyclonal antibody, or a recombinant antibody. Furthermore, the ELISA kit may comprise an antibody specific to a control protein. In addition, the ELISA kit may further comprise reagents capable of detecting the bound antibody, for example, a labeled secondary antibody, chromophores, an enzyme (e.g., conjugated with the antibody) and a substrate thereof, or other substance capable of binding to the antibody.

In the kit for diagnosing anticancer drug resistance according to the present invention, a fixture for antigen-antibody binding reaction may be a well plate synthesized from a nitrocellulose membrane, a PVDF membrane, a polyvinyl resin or a polystyrene resin, or a glass slide made of glass, without being limited thereto.

In the kit for diagnosing anticancer drug resistance according to the present invention, a label for the secondary antibody is preferably a conventional chromogenic agent for color development, and examples of the label include, but are not limited to, fluoresceins such as HRP (horseradish peroxidase), alkaline phosphatase, colloid gold, FITC (poly L-lysine-fluorescein isothiocyanate), RITC (rhodamine-B-isothiocyanate), and dyes.

In the kit for diagnosing anticancer drug resistance according to the present invention, a chromogenic substrate for inducing the chromogenic reaction is preferably selected depending on the chromogenic label, and may be TMB (3,3',5,5'-tetramethyl benzidine), ABTS [2,2'-azino-bis(3-ethylbenzothiazoline-6-sulfonic acid)], or OPD (o-phenylenediamine). In this case, the chromogenic substrate is more preferably provided as dissolved in buffer (0.1M NaAc, pH 5.5). A chromogenic substrate such as TMB is degraded by HRP, used as a label for the secondary antibody conjugate, to form a chromogen, and the presence of the marker protein is detected by visually checking the degree of deposition of the chromogen.

The washing solution in the kit for diagnosing anticancer drug resistance according to the present invention preferably comprises phosphate buffer, NaCl and Tween 20. More preferably, the washing solution is a buffer solution (PBST) consisting of 0.02 M phosphate buffer, 0.13 M NaCl, and 0.05% Tween 20. After the antigen-antibody binding reaction, the secondary antibody is allowed to react with the antigen-antibody complex, and then the resulting conjugate is washed 3 to 6 times with a suitable amount of the washing solution added to the fixture. As the reaction stop solution, a sulfuric acid ($H_2SO_4$) solution may be preferably used.

Still another embodiment of the present invention is directed to a method for providing information for diagnosing anticancer drug resistance.

The method of the present invention may comprise a step of measuring the expression level of the NINJ2 protein, or a gene encoding the protein, in a biological sample isolated from a subject of interest.

The method of the present invention may be intended to screen the presence or absence of anticancer drug resistance in the biological sample isolated from the subject of interest.

In the present invention, the "subject of interest" refers to a subject having or being likely to develop cancer, and may be a mammal including a human. For example, the subject of interest may be selected from the group consisting of a human, a rat, a mouse, a guinea pig, a hamster, a rabbit, a monkey, a dog, a cat, a cow, a horse, a pig, sheep, and a goat. Preferably, the subject of interest may be a human, without being limited thereto.

In the present invention, the "biological sample" refers to any material, biological fluid, tissue or cells obtained or derived from the subject. For example, the biological sample may be at least one selected from the group consisting of whole blood, leukocytes, peripheral blood mononuclear cells, buffy coat, plasma, serum, sputum, tears, mucus, nasal washes, nasal aspirate, breath, urine, semen, saliva, peritoneal washings, ascites, cystic fluid, meningeal fluid, amniotic fluid, glandular fluid, pancreatic fluid, lymph fluid, pleural fluid, nipple aspirate, bronchial aspirate, synovial fluid, joint aspirate, organ secretions, cells, cell extract, or cerebrospinal fluid, without being limited thereto.

In the present invention, the method may further comprise a step of measuring the expression level of at least one protein selected from among periostin and CD44, or a gene encoding at least one protein.

In the present invention, the agent for measuring the expression level of the protein may comprise at least one selected from the group consisting of an antibody, an oligopeptide, a ligand, a peptide nucleic acid (PNA) and an aptamer, which specifically bind to the protein.

In the present invention, measurement of the expression level of the protein may be performed by protein chip assay, immunoassay, ligand binding assay, MALDI-TOF (Matrix Assisted Laser Desorption/Ionization Time of Flight Mass Spectrometry) assay, SELDI-TOF (Surface Enhanced Laser Desorption/Ionization Time of Flight Mass Spectrometry) assay, radioimmunoassay, radioimmunodiffusion, Ouchterlony immunodiffusion, rocket immunoelectrophoresis, immunohistochemical staining, complement fixation assay, two-dimensional electrophoresis assay, liquid chromatography-mass spectrometry (LC-MS), LC-MS/MS (liquid chromatography-mass spectrometry/mass spectrometry), Western blotting, or ELISA (enzyme-linked immunosorbent assay).

In addition, in the present invention, measurement of the expression level of the protein may be performed by a multiple-reaction monitoring (MRM) method.

In the present invention, either a synthetic peptide obtained by substituting specific amino acids of the target peptide with an isotope, or *E. coli* beta-galactosidase, may be used as an internal standard substance in the multiple-reaction monitoring method.

In the present invention, the NINJ2 protein may consist of the amino acid sequence shown in SEQ ID NO: 1 or SEQ ID NO: 2, without being limited thereto.

In the present invention, the periostin protein may consist of the amino acid sequence shown in SEQ ID NO: 7, without being limited thereto.

In the present invention, the CD44 protein may consist of the amino acid sequence shown in SEQ ID NO: 8, without being limited thereto.

In the present invention, the agent for measuring the expression level of the gene encoding the protein may comprise at least one selected from the group consisting of a primer, a probe and an antisense nucleotide, which bind specifically to the gene encoding the protein.

In the present invention, measurement of the expression level of the gene encoding the protein may be performed by reverse transcription-polymerase chain reaction (RT-PCR), competitive RT-PCR, real-time RT-PCR, RNase protection assay (RPA), Northern blotting, or DNA chip assay.

In the present invention, the gene encoding the NINJ2 protein may consist of the nucleotide sequence shown in SEQ ID NO: 3 or SEQ ID NO: 4, without being limited thereto.

In the method for providing information according to the present invention, the antibody, the oligopeptide, the ligand, the peptide nucleic acid (PNA), the aptamer, the primer, the probe, and the like overlap with those described above, and thus detailed description thereof will be omitted in order to avoid excessive complexity of the present specification.

In the present invention, when the measured expression level of either the NINJ2 protein or the gene encoding the same in the biological sample isolated from the subject of interest is higher than that in a control, it may be predicted that the subject of interest has anticancer drug resistance or a high likelihood of developing anticancer drug resistance, and thus it may be predicted that the therapeutic responsiveness of the subject to the anticancer drug is low or the prognosis of cancer treatment in the subject will be poor.

In the present invention, in addition to when the measured expression level of either the NINJ2 protein or the gene encoding the same in the biological sample isolated from the subject of interest is higher than that in a control, when the expression level of either at least one protein selected from among periostin and CD44 proteins or a gene encoding at least one protein is higher than that in the control, it may be predicted that the subject of interest has anticancer drug resistance or a high likelihood of developing anticancer drug resistance, and thus it may be predicted that the therapeutic responsiveness of the subject to the anticancer drug is low or the prognosis of cancer treatment in the subject will be poor.

In the present invention, the "control" may be either a normal control in which anticancer drug resistance has not occurred, or the average or median value of the expression level of the NINJ2 protein or the gene encoding the same in anticancer drug-sensitive cells. The expression level of the marker protein or the nucleic acid molecule encoding the same in the control may be compared with the expression level of the marker protein or the nucleic acid molecule encoding the same in the cancer patient-derived biological sample to be analyzed, and the presence or absence of anticancer drug resistance may be diagnosed by determining whether the change in the expression level is significant. The scope of the normal control sample also includes cells derived from a cancer patient confirmed not to have acquired resistance to the anticancer drug of interest, and a culture of the cells, as well as the blood, serum, plasma and tissue derived from the cancer patient.

In the present invention, the anticancer drug may be a drug comprising at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, and carmustine. Preferably, the anticancer drug may be a drug comprising at least one selected from the group consisting of epirubicin, cisplatin and 5-fluorouracil, and more preferably, may be a combination of ECF comprising epirubicin, cisplatin and 5-fluorouracil. In addition, the anticancer drug is not limited thereto and may comprise any drug belonging to the same family as ECF.

In the present invention, the cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, CNS central nervous system tumor, primary CNS lymphoma, spinal cord tumor, brainstem glioma, or pituitary adenoma. However, the cancer is not limited thereto and may be any type of cancer in which cancer progression, such as tumor differentiation and/or proliferation, is dependent on cancer cells and/or cancer stem cells as described in the present invention 2. Use of Treatment of Cancer and Treatment of Anticancer Drug Resistance Yet another embodiment of the present invention is directed to a pharmaceutical composition for preventing or treating cancer.

In the composition of the present invention, the cancer is a cancer that has developed or is likely to develop in the subject of interest. Preferably, the cancer may be a cancer in which the expression level of the NINJ2 protein or a gene encoding the same is higher than the control, without being limited thereto. Here, the control may be either the expression level of the NINJ2 protein or the gene encoding the same in the corresponding tissue of a normal individual, or the average value or median value thereof, or the expression level of the NINJ2 protein or the gene encoding the same in cancer or the corresponding cancer, or the average value or median value thereof, without being limited thereto.

In the present invention, the cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, CNS central nervous system tumor, primary CNS lymphoma, spinal cord tumor, brainstem glioma, or pituitary adenoma. However, the cancer is not limited thereto and may be any type of cancer in which cancer progression, such as tumor differentiation and/or proliferation, is dependent on cancer cells and/or cancer stem cells as described in the present invention.

As used herein, the term "preventing" may include, without limitation, any action of blocking symptoms caused by the uncontrolled growth of cancer cells or suppressing or delaying the symptoms, by using the composition of the present invention.

As used herein, the term "treating" may include, without limitation, any action of alleviating or beneficially changing symptoms caused by the uncontrolled growth of cancer cells by using the composition of the present invention.

The composition of the present invention may contain, as an active ingredient: an agent for reducing the activity or expression level of the NINJ2 protein; or an agent for reducing the expression level of the gene encoding the protein.

In the present invention, the NINJ2 protein may consist of the amino acid sequence shown in SEQ ID NO: 1 or SEQ ID NO: 2, and the gene encoding the NINJ2 protein may consist of the nucleotide sequence shown in SEQ ID NO: 3 or SEQ ID NO: 4, without being limited thereto.

The composition of the present invention may further contain an agent for reducing the activity or expression level of at least one protein selected from among periostin and CD44, or an agent for reducing the expression level of the gene encoding at least one protein.

In the present invention, the periostin protein may consist of the amino acid sequence shown in SEQ ID NO: 7, without being limited thereto.

In the present invention, the CD44 protein may consist of the amino acid sequence shown in SEQ ID NO: 8, without being limited thereto.

The agent for reducing the activity or expression level of the protein according to the present invention may comprise any one or more selected from the group consisting of compounds, peptides, peptide mimetics, aptamers, antibodies, and natural products, which specifically bind to the protein or a portion thereof, without being limited thereto. However, the agent for reducing the activity or expression level of the protein is not limited thereto and may include any agent, which exhibits the effect of inhibiting the activity or expression of the target NINJ2 protein by direct or indirect action thereon and may be easily obtained by a known technique using a method that is commonly used in the art.

In the present invention, the "peptide mimetics" is a peptide or non-peptide that inhibits the binding domain of the NINJ2 protein leading to the inhibition of NINJ2 activity. Major residues of a nonhydrolyzable peptide analog may be produced by using β-turn dipeptide cores (Nagai et al. Tetrahedron Lett 26:647, 1985), keto methylene pseudopeptides (Ewenson et al. J Med Chem 29:295, 1986; and Ewenson et al. in Peptides: Structure and Function (Proceedings of the 9th American Peptide Symposium) Pierce Chemical co. Rockland, IL, 1985), azepine (Huffman et al. in Peptides: Chemistry and Biology, G. R. Marshall ed., ESCOM Publisher: Leiden, Netherlands, 1988), benzodiazepine (Freidinger et al. in Peptides; chemistry and Biology, G. R. Marshall ed., ESCOM Publisher: Leiden, Netherlands, 1988), β-aminoalcohol (Gordon et al. Biochem Biophys Res commun 126:419 1985), and a substituted gamma-lactam ring (Garvey et al. in Peptides: chemistry and Biology, G. R. Marshell ed., ESCOM Publisher: Leiden, Netherlands, 1988).

In the present invention, the "aptamer" is a single-stranded nucleic acid (DNA, RNA or modified nucleic acid) that has its own stable tertiary structure and is capable of binding to a target molecule with high affinity and specificity. Since the aptamer discovery technology called SELEX (Systematic Evolution of Ligands by EXponential enrichment) was first developed (Ellington, A D and Szostak, J W., Nature 346:818-822, 1990), many aptamers that can bind to various target molecules, including organic small molecules, peptides, and membrane proteins, have been continuously discovered. The aptamer is comparable to a monoclonal antibody due to its characteristic capable of binding to a target molecule with unique high affinity (usually a pM level) and specificity, and has high potential as an alternative antibody, particularly as a "chemical antibody".

In the present invention, the "antibody" may be produced through injection of the protein or is commercially available. Furthermore, the antibodies include a polyclonal antibody, a monoclonal antibody, and a fragment capable of binding to an epitope.

Here, the polyclonal antibody may be produced by a conventional method of obtaining serum containing the antibody by injecting the protein into an animal and collecting blood from the corresponding animal. This polyclonal antibody may be purified by any method known in the art and made from any animal species host, such as goats, rabbits, sheep, monkeys, horses, pigs, cows, dogs, and the like.

The monoclonal antibody may be produced using any technology that provides the production of antibody molecules through the cultivation of continuous cell lines. Such technologies include, but are not limited, hybridoma technology, human B-cell line hybridoma technology, and EBV-hybridoma technology.

Furthermore, antibody fragments containing specific binding sites for the protein may be produced. For example, F(ab')2 fragments may be produced by degrading an antibody molecule with pepsin, and Fab fragments may be produced by reducing disulfide bridges of the F(ab')2 fragments, without being limited thereto. Alternatively, monoclonal Fab fragments having desired specificity may be identified quickly and easily by decreasing a Fab expression library.

In the present invention, the antibody may be bound to a solid substrate to facilitate subsequent steps such as washing or separation of the complex. Examples of the solid substrate include a synthetic resin, nitrocellulose, a glass substrate, a metal substrate, glass fibers, microspheres, microbeads, and the like. In addition, examples of the synthetic resin include polyester, polyvinyl chloride, polystyrene, polypropylene, PVDF, nylon, and the like.

In the present invention, the agent for reducing the activity or expression level of the protein may specifically bind to the polypeptide of NINJ2 protein shown in SEQ ID NO: 1 or SEQ ID NO: 2. Preferably, the composition of the present invention may contain an antibody specific for the NINJ2 protein, wherein the antibody may specifically bind to the polypeptide shown in SEQ ID NO: 1 or SEQ ID NO: 2, without being limited thereto.

The agent for reducing the expression level of the gene encoding the protein according to the present invention may comprise any one or more selected from the group consisting of an antisense nucleotide, a short interfering RNA (siRNA), a short hairpin RNA, and ribozyme, which bind complementarily to the gene encoding the protein, preferably the gene or a portion thereof, without being limited thereto. However, the agent for reducing the expression level of the gene is not limited thereto and may include any agent, which exhibits the effect of inhibiting the expression of the gene encoding the target NINJ2 protein by direct or indirect action thereon and may be easily obtained by a known technique using a method that is commonly used in the art.

In one example of the present invention, the agent for reducing the expression level of the gene encoding the NINJ2 protein according to the present invention may comprise any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6, which is a portion of the gene encoding the NINJ2 protein, without being limited thereto.

In the present invention, the antisense nucleotide binds (hybridizes) to a complementary nucleotide sequence of DNA, immature-mRNA, or mature mRNA as defined in a Watson-click base pair, to interrupt the transmission of genetic information as a protein in DNA. The nature of antisense nucleotides specific to a target sequence makes them exceptionally versatile. Since the antisense nucleotides are long chains of monomer units, the antisense nucleotides may be easily synthesized with respect to the target RNA sequence. Many recent studies have verified the utility of antisense nucleotides as biochemical means for studying target proteins. Since there has been much progress in the fields of oligonucleotide chemistry and nucleotide synthesis having improved cell line adsorption, target binding affinity and nuclease resistance, the use of the antisense nucleotide may be considered as a novel type of inhibitor.

In the present invention, the "shRNA" and "siRNA" are nucleic acid molecules capable of mediating RNA interference or gene silencing, can inhibit the expression of a target gene, and thus are used as an efficient gene knockdown method or gene therapy method. shRNA has a hairpin structure formed by binding between complementary sequences within a single-stranded oligonucleotide. In vivo, the shRNA may be cleaved by a dicer into the double-stranded oligonucleotide siRNA, which is a short RNA fragment of 21 to 25 nucleotides in length, and may bind specifically to an mRNA having a complementary sequence and inhibit the expression of the mRNA. In addition, siRNA refers to a short double-stranded RNA (dsRNA) fragment of 21 to 25 nucleotides in length, which induces RNA interference (RNAi) by modifying the target mRNA.

In the present invention, which one of the shRNA and siRNA to use may be determined by a person skilled in the art, and if the mRNA sequences targeted by them are the same, a similar expression reduction effect can be expected. With regard to the purposes of the present invention, siRNA may act specifically on the NINJ2-encoding gene to cleave the NINJ2 gene (e.g., an mRNA molecule) and RNA interference (RNAi), thereby inhibiting expression of the NINJ2 protein. siRNA can be synthesized chemically or enzymatically. The method for producing siRNA is not particularly limited, and a method known in the art may be used to produce siRNA. Examples of the method for producing siRNA include, but are not limited to, a method of directly chemically synthesizing siRNA, a method of synthesizing siRNA using in vitro transcription, a method of enzymatically cleaving a long double-stranded RNA synthesized by in vitro transcription, an expression method through intracellular delivery of an shRNA expression plasmid or viral vector, and an expression method through intracellular delivery of a PCR (polymerase chain reaction)-induced siRNA expression cassette.

In one example of the present invention, the agent for reducing the expression level of the gene encoding the NINJ2 protein may be an shRNA consisting of the nucleotide sequence shown in SEQ ID NO: 9 or 10, without being limited thereto.

In another example of the present invention, the agent for reducing the expression level of the gene encoding the NINJ2 protein may be an siRNA consisting of the nucleotide sequences shown in SEQ ID NOs: 11 and 12, without being limited thereto.

In the present invention, the "ribozyme" refers to an RNA molecule having catalytic activity. Ribozymes having various activities are known, and ribozymes of the NINJ2 gene include known ribozymes or artificially generated ribozymes. Alternatively, ribozymes having target-specific RNA cleavage activity may be produced by a known standard technique.

Still yet another embodiment of the present invention is directed to a pharmaceutical composition for treating anticancer drug resistance or enhancing anticancer drug sensitivity.

The pharmaceutical composition for treating anticancer drug resistance or enhancing anticancer drug sensitivity according to the present invention may contain, as an active ingredient, an agent for reducing the activity or expression level of the NINJ2 protein, or an agent for reducing the expression level of a gene encoding the protein.

In one example of the present invention, the agent for reducing the expression level of the gene encoding the NINJ2 protein may comprise any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6, which is a portion of the gene encoding the NINJ2 protein, without being limited thereto.

The composition of the present invention may further contain an agent for reducing the activity or expression level of at least one protein selected from among periostin and CD44, or an agent for reducing the expression level of the gene encoding at least one protein.

In the present invention, the term "anticancer drug resistance" means that the effect of an anticancer drug decreases when the anticancer drug is used quantitatively and repeatedly, and refers to a condition in which the frequency of use of an anticancer drug or the amount of anticancer drug used needs to be increased to obtain the same effect as previously experienced by the patient resistant to the anticancer drug, or a condition in which the same effect as before is not obtained even when the same dose of the anticancer drug as before is administered.

In the present invention, the term "treatment of anticancer drug resistance" refers to recovery from a condition in which the effect of an anticancer drug decreases when the anticancer drug is used quantitatively and repeatedly, or a condition in which the frequency of use of an anticancer drug or the amount of anticancer drug used needs to be increased to obtain the same effect as previously experienced by the patient resistant to the anticancer drug, or a condition in which the same effect as before is not obtained even when the same dose of the anticancer drug as before is administered. More specifically, the term "treatment of anticancer drug resistance" refers to creating a condition in which the same anticancer effect appears even when the anticancer drug is applied less frequently or at a lower dose, or a condition which is prior to the occurrence of anticancer drug resistance and in which the same effect can be obtained even when the anticancer drug is administered at the same dose or lower dose than before.

In the present invention, the anticancer drug may be a drug comprising at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, and carmustine. Preferably, the anticancer drug may be a drug comprising at least one selected from the group consisting of epirubicin, cisplatin and 5-fluorouracil, and more preferably, may be a combination of ECF comprising epirubicin, cisplatin and 5-fluorouracil. In addition, the anticancer drug is not limited thereto and may comprise any drug belonging to the same family as ECF.

In the present invention, the cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, CNS central nervous system tumor, primary CNS lymphoma, spinal cord tumor, brainstem glioma, or pituitary adenoma. However, the cancer is not limited thereto and may be any type of cancer in which cancer progression, such as tumor differentiation and/or proliferation, is dependent on cancer cells and/or cancer stem cells as described in the present invention.

In the pharmaceutical composition for treating anticancer drug resistance and the composition for enhancing anticancer drug sensitivity according to the present invention, each protein or a gene encoding the same, the agent for reducing the activity or expression level of the protein, or the agent for reducing the expression level of the gene encoding the protein is the same as described above with respect to in the pharmaceutical composition for preventing or treating cancer, and thus detailed description thereof will be omitted in order to avoid excessive complexity of the present specification.

A further embodiment of the present invention is directed to a pharmaceutical composition for preventing or treating anticancer drug-resistant cancer.

The composition of the present invention may contain, as an active ingredient, an agent for reducing the activity or expression level of NINJ2 protein, or an agent for reducing the expression level of a gene encoding the protein.

In one example of the present invention, the agent for reducing the expression level of the gene encoding the NINJ2 protein may comprise any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6, which is a portion of the gene encoding the NINJ2 protein, without being limited thereto.

The composition of the present invention may further contain an agent for reducing the activity or expression level of at least one protein selected from among periostin and CD44, or an agent for reducing the expression level of the gene encoding at least one protein.

The composition of the present invention is capable of very effectively treating anticancer drug-resistant cancer having anticancer drug resistance. The composition of the present invention may be very effectively used to prevent, alleviate or treat cancer by lowering the anticancer drug resistance of cancer having anticancer drug resistance and at the same time, enhancing the anticancer drug sensitivity of the cancer.

In the present invention, the anticancer drug may be a drug comprising at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, and carmustine. Preferably, the anticancer drug may be a drug comprising at least one selected from the group consisting of epirubicin, cisplatin and 5-fluorouracil, and more preferably, may be a combination of ECF comprising epirubicin, cisplatin and 5-fluorouracil. In addition, the anticancer drug is not limited thereto and may comprise any drug belonging to the same family as ECF.

In the present invention, the cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, CNS central nervous system tumor, primary CNS lymphoma, spinal cord tumor, brainstem glioma, or pituitary adenoma. However, the cancer is not limited thereto and may be any type of cancer in which cancer progression, such as tumor differentiation and/or proliferation, is dependent on cancer cells and/or cancer stem cells as described in the present invention.

In the pharmaceutical composition for preventing or treating anticancer drug-resistant cancer according to the present invention, each protein or a gene encoding the same, the agent for reducing the activity or expression level of the protein, or the agent for reducing the expression level of the gene encoding the protein is the same as described above with respect to the composition for preventing or treating cancer, and thus detailed description thereof will be omitted in order to avoid excessive complexity of the present specification.

In the present invention, the pharmaceutical composition may be in the form of capsules, tablets, granules, injectable solutions, ointments, powders or beverages. The pharmaceutical composition may be for administration to humans.

For use, the pharmaceutical composition of the present invention may be formulated as oral preparations, including powders, granules, capsules, tablets, aqueous suspensions and the like, skin external preparations, suppositories, and sterile injectable solutions, according to conventional methods, without being limited thereto. The pharmaceutical composition of the present invention may contain a pharmaceutically acceptable carrier. Examples of pharmaceutically acceptable carriers that may be used in the present invention include binders, lubricants, disintegrants, excipients, solubilizers, dispersing agents, stabilizers, suspending agents, pigments, fragrances and the like, which may be used for oral administration; buffers, preservatives, pain-relieving agents, solubilizers, isotonic agents, stabilizers and the like, which may be used for injection; and bases, excipients, lubricants, preservatives and the like, which may be used for local administration. The pharmaceutical composition of the present invention may be formulated in various ways by mixing it with the pharmaceutically acceptable carrier as described above. For example, for oral administration, the pharmaceutical composition of the present invention may be formulated as tablets, troches, capsules, elixirs, suspensions, syrups, wafers or the like, and for injection, may be formulated as unit dose ampoules or multi-dose vials. In addition, the pharmaceutical composition of the present invention may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present invention may further contain a filler, an anticoagulant, a lubricant, a wetting agent, a fragrance, an emulsifier, a preservative or the like.

The routes of administration of the pharmaceutical composition according to the present invention include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

As used herein, the term "parenteral" is meant to include subcutaneous, transdermal, intravenous, intramuscular, intra-articular, intra-synovial, intrasternal, intradural, intralesional and intra-cranial injection or infusion techniques. Preferably, the pharmaceutical composition of the present invention may also be formulated as suppositories for intrarectal administration, without being limited thereto.

The pharmaceutical composition of the present invention may vary depending on various factors, including the activity of specific compounds used, the patient's age, body weight, general health, sex, and diet, the period of administration, the route of administration, excretion rate, the drug content, and the severity of a specific disease to be prevented or treated. The dose of the pharmaceutical composition may be suitably selected by a person skilled in the art depending on the patient's condition and body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present invention in any way. The pharmaceutical composition according to the present invention may be formulated as pills, sugar-coated tablets, capsules, liquids, gels, syrups, slurries, or suspensions.

Another further embodiment of the present invention is directed to a method for preventing or treating cancer.

The method of the present invention may comprise a step of administering, to a subject in need thereof, an effective amount of either an agent for reducing the activity or expression level of NINJ2 (nerve injury-induced protein 2; Ninjurin 2) protein, or an agent for reducing the expression level of a gene encoding the protein. In one example of the present invention, the method may comprise a step of administering an effective amount of any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6, which is a portion of the gene encoding the NINJ2 protein, without being limited thereto.

Still another further embodiment of the present invention is directed to a method for preventing or treating anticancer drug-resistant cancer.

The method of the present invention may comprise a step of administering, to a subject in need thereof, an effective amount of either an agent for reducing the activity or expression level of NINJ2 (nerve injury-induced protein 2; Ninjurin 2) protein, or an agent for reducing the expression level of a gene encoding the protein.

The method of the present invention may comprise a step of administering, to a subject in need thereof, an effective amount of either an agent for reducing the activity or expression level of NINJ2 (nerve injury-induced protein 2; Ninjurin 2) protein, or an agent for reducing the expression level of a gene encoding the protein.

In one example of the present invention, the method may comprise a step of administering an effective amount of any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6, which is a portion of the gene encoding the NINJ2 protein, without being limited thereto.

Yet another further embodiment of the present invention is directed to a method for treating anticancer drug resistance or enhancing anticancer drug sensitivity.

The method of the present invention may comprise a step of administering, to a subject in need thereof, an effective amount of either an agent for reducing the activity or expression level of NINJ2 (nerve injury-induced protein 2; Ninjurin 2) protein, or an agent for reducing the expression level of a gene encoding the protein.

In one example of the present invention, the method may comprise a step of administering an effective amount of any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6, without being limited thereto.

In the method for preventing or treating cancer, the method for preventing or treating anticancer drug-resistant cancer, the method for enhancing anticancer drug sensitivity, and the method for treating anticancer cancer resistance, according to the present invention, each protein or a gene encoding the same, the agent for reducing the activity or expression level of the protein, or the agent for reducing the expression level of the gene encoding the protein, and the antisense nucleotide, the short interfering RNA (siRNA), the short hairpin RNA and the ribozyme, which bind complementarily to a polynucleotide consisting of the nucleotide sequence shown in SEQ ID NO: 5 or 6, are the same as described above with respect to the pharmaceutical composition for preventing or treating cancer, and thus detailed description thereof will be omitted in order to avoid excessive complexity of the present specification.

As used herein, the term "administering" means providing a certain composition of the present invention to a subject by any suitable method.

In the present invention, the "subject" in need of administration may include both mammals and non-mammals. Here, examples of the mammals include, but are not limited to, humans, nonhuman primates such as chimpanzees, other apes or monkey species; livestock animals such as cattle, horses, sheep, goats, or pigs; domestic animals such as rabbits, dogs or cats; laboratory animals such as rodents, for example, rats, mice or guinea pigs. In addition, in the present invention, examples of the non-mammals include, but are not limited to, birds or fish.

In the present invention, the formulation of the composition that is administered as described above is not particularly limited. The composition may be administered as solid form preparations, liquid form preparations, or aerosol preparations for inhalation. Specifically, the composition may be administered as solid form preparations which are intended to be converted into liquid form preparations for oral or parenteral administration shortly before use. For example, the composition may be formulated and administered as oral preparations such as powders, granules, capsules, tablets or aqueous suspensions, as well as external preparations, suppositories, or sterile injection solutions, without being limited thereto.

In addition, in the present invention, a pharmaceutically acceptable carrier may be additionally administered together with the composition of the present invention. Pharmaceutically acceptable carriers that may be used in the present invention include binders, lubricants, disintegrants, excipients, solubilizers, dispersing agents, stabilizers, suspending agents, colorants, fragrances and the like, which may be used for oral administration; buffers, preservatives, pain-relieving agents, solubilizers, isotonic agents, stabilizers and the like, which may be used for injection; and bases, excipients, lubricants, preservatives and the like, which may be used for local administration. The composition of the present invention may be formulated in various ways by mixing it with the pharmaceutically acceptable carrier as described above. For example, for oral administration, the composition of the present invention may be formulated as tablets, troches, capsules, elixirs, suspensions, syrups, wafers or the like, and for injection, may be formulated as unit dose ampoules or multi-dose vials. In addition, the composition of the present invention may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present invention may further contain a filler, an anticoagulant, a lubricant, a wetting agent, a fragrance, an emulsifier, a preservative, and the like.

The routes of administration of the composition according to the present invention include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

As used herein, the term "parenteral" is meant to include subcutaneous, transdermal, intravenous, intramuscular, intra-articular, intra-synovial, intrasternal, intradural, intralesional and intra-cranial injection or infusion techniques. Preferably, the pharmaceutical composition of the present invention may also be formulated as suppositories for intrarectal administration, without being limited thereto.

As used herein, the "pharmaceutically effective amount" refers to a sufficient amount of an agent to provide the desired biological result. That result may be reduction and/or alleviation of the signs, symptoms, or causes of a disease, or any other desired alteration of a biological system. For example, an "effective amount" for therapeutic uses is the amount of the composition disclosed herein required to provide a clinically significant reduction in the disease. An appropriate effective amount in any individual case may be determined by one of ordinary skill in the art using routine experimentation. Thus, the expression "effective amount" generally refers to an amount in which the active substance has a therapeutic effect. In the case of the present invention, the active substance is an agent for preventing, ameliorating or treating cancer, and at the same time, an agent for preventing, ameliorating or treating anticancer drug-resistant cancer.

The composition of the present invention may vary depending on various factors, including the activity of the active substance used, the patient's age, body weight, general health, sex and diet, the period of administration, the route of administration, excretion rate, the drug content, and the severity of a specific disease to be prevented or treated. The dose of the active substance may be suitably selected by a person skilled in the art depending on the patient's condition and body weight, the severity of the disease, the form of drug, and the route and period of administration, and may be 0.0001 to 100 mg/kg/day or 0.001 to 100 mg/kg/day. The composition may be administered once or several times a day. The dose is not intended to limit the scope of the present invention in any way. The composition according to the present invention may be formulated as pills, sugar-coated tablets, capsules, liquids, gels, syrups, slurries, or suspensions.

The active substance of the present invention may be used alone or in combination with surgery, radiotherapy, hormone therapy, chemotherapy, and methods employing biological response modifiers.

In addition, the composition of the present invention may also be used in combination with other anticancer drug. Here, the anticancer drug may be at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, sorafenib, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, capecitabine, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, vorinostat, entinostat, phenformin, metformin, talazoparib, and carmustine, without being limited thereto.

3. Anticancer Drug-Resistant Cancer Organoid

Still yet another further embodiment of the present invention is directed to an anticancer drug-resistant cancer organoid.

In the present invention, the cancer organoid comprises cancer cells expressing NINJ2 protein or a gene encoding the same.

In the present invention, the NINJ2 protein may be at least one of NINJ2 isoform 1 consisting of the amino acid sequence shown in SEQ ID NO: 1 and NINJ2 isoform 3 consisting of the amino acid sequence shown in SEQ ID NO: 2.

In the present invention, the gene encoding the NINJ2 protein may be at least one of an NINJ2 isoform 1 gene consisting of the nucleotide sequence shown in SEQ ID NO: 3 and an NINJ2 isoform 3 gene consisting of the nucleotide sequence shown in SEQ ID NO: 4.

In the present invention, the cancer cells may additionally express either at least one protein selected from periostin and CD44, or a gene encoding at least one protein.

In the present invention, the periostin protein may consist of the amino acid sequence shown in SEQ ID NO: 7, without being limited thereto.

In the present invention, the CD44 protein may consist of the amino acid sequence shown in SEQ ID NO: 8, without being limited thereto.

In the present invention, the cancer cells may be engineered to overexpress the protein or the gene encoding the protein, and preferably, may be transfected by introducing a recombinant vector containing the gene encoding the protein into the cancer cells.

As used herein, the term "vector" refers to a means for expressing the gene of interest in a host cell. The vector may comprise elements for expression of the gene of interest, including a replication origin, a promoter, an operator, a transcription terminator, and the like, and may further comprise appropriate enzyme sites (e.g., restriction enzyme sites) for introduction into the genome of a host cell, and/or a selection marker for identifying successful introduction into the host cell, and/or a ribosome binding site (RBS), an internal ribosome entry site (IRES) and the like for translation into protein. The vector may be engineered by a conventional genetic engineering method so as to have the above-described fusion polynucleotide (fusion promoter) as a promoter. The vector may further comprise a transcriptional control sequence (e.g., an enhancer, etc.) other than the promoter.

In the present invention, the recombinant vector may be a viral or non-viral vector. The viral vector may be an adenoviral vector, a retroviral vector including a lentivirus, an adeno-associated viral vector, or a herpes simplex virus vector, without being limited thereto. In addition, the non-viral vector may be a plasmid vector, a bacteriophage vector, a liposome, a bacterial artificial chromosome, an artificial yeast chromosome, or the like, without being limited thereto.

In the present invention, the gene of interest in the recombinant vector may be operatively linked to the fusion polynucleotide. The term "operatively linked" refers to a functional linkage between a gene expression control sequence and another nucleotide sequence. The gene expression control sequence may be "operatively linked" to control the transcription and/or translation of other nucleotide sequences. In the recombinant vector, the fusion polynucleotide may be linked to the 5' end of the gene of interest so that the fusion polynucleotide is operatively linked to the gene of interest. The recombinant vector of the present invention may be used as a target protein expression vector capable of expressing a protein of interest with high efficiency in an appropriate host cell, when the gene encoding the protein of interest to be expressed is operably linked.

The recombinant vector of the present invention may further comprise a transcriptional control sequence. The transcriptional control sequence may be at least one selected from the group consisting of a transcription termination sequence such as a polyadenylation sequence (pA), and replication origins such as an f1 replication origin, an SV40 replication origin, a pMB1 replication origin, an adeno replication origin, an AAV replication origin, and a BBV replication origin, without being limited thereto.

In addition, in the present invention, the recombinant vector may further comprise a selection marker. The selection marker is a gene for confirming whether the recombinant vector has been successfully introduced into a host cell or for constructing a stable cell line. For example, the selection marker may be at least one selected from the group consisting of drug resistance genes such as antibiotics, metabolism-related genes, gene-amplifying genes, and the like.

In the present invention, the delivery (introduction) of the recombinant vector into cancer cells may be performed using a delivery method well known in the art. The delivery method may be, for example, microinjection, calcium phosphate precipitation, electroporation, sonoporation, magnetofection, liposome-mediated transfection, gene bombardment, or a method employing dendrimers and inorganic nanoparticles, without being limited thereto.

In the present invention, the anticancer drug may be a drug comprising at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, and carmustine. Preferably, the anticancer drug may be a drug comprising at least one selected from the group consisting of epirubicin, cisplatin and 5-fluorouracil, and more preferably, may be a combination of ECF comprising epirubicin, cisplatin and 5-fluorouracil. In addition, the anticancer drug is not limited thereto and may comprise any drug belonging to the same family as ECF.

In the present invention, the cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, CNS central nervous system tumor, primary CNS lymphoma, spinal cord tumor, brainstem glioma, or pituitary adenoma. However, the cancer is not limited thereto and may be any type of cancer in which cancer progression, such as tumor differentiation and/or proliferation, is dependent on cancer cells and/or cancer stem cells as described in the present invention.

In the present invention, cancer cells expressing the NINJ2 protein or the gene encoding the protein may show resistance to anticancer drugs. Thus, with regard to the purposes of the present invention, the cancer cells may form cancer organoids that may be used to screen either drugs for overcoming or treating anticancer drug resistance, or drugs capable of enhancing anticancer drug sensitivity.

As used herein, the term "organoid" refers to cells having a 3D structure, and means a tissue-like model prepared through an artificial culture process, which is not collected or obtained from animals. Unlike 2D culture, 3D cell culture allows cells to grow in all directions in vitro.

4. Method for Screening Drug for Overcoming or Treating Anticancer Drug Resistance or Drug for Enhancing Anticancer Drug Sensitivity Still further embodiment of the present invention is directed to a method for screening a drug for overcoming or treating anticancer drug resistance or a drug for enhancing anticancer drug sensitivity.

The screening method according to the present invention may comprise steps of: treating either cancer cells expressing NINJ2 protein or a gene encoding the same, or a cancer organoid provided by the present invention, with a candidate substance in vitro; and measuring the activity or expression level of the NINJ2 protein or measuring the expression level of the gene encoding the protein, in the cancer cells or the cancer organoid after treatment with the candidate substance.

In the present invention, the term "screening" refers to selecting a substance having any desired specific property from a candidate group consisting of several substances by a specific manipulation or evaluation method.

In the present invention, the cancer cells may be isolated from a subject of interest, preferably a subject having or being likely to have anticancer drug resistance, or may be engineered to overexpress the NINJ2 protein or the gene encoding the protein. Preferably, the cancer cells may be transfected by introducing a recombinant vector containing the gene encoding the NINJ2 protein into the cancer cells.

In addition, in the present invention, the cancer cells may further express at least one of CD44 and periostin proteins or a gene encoding at least one protein, or may be engineered to overexpress at least one of CD44 and periostin proteins or a gene encoding at least one protein. Preferably, the cancer cells may be transfected by introducing a recombinant vector containing the gene encoding at least one of CD44 and periostin proteins into the cancer cells.

In the present invention, the candidate substance may be at least one selected from the group consisting of natural compounds, synthetic compounds, RNA, DNA, polypeptides, enzymes, proteins, ligands, antibodies, antigens, bacterial or fungal metabolites, and bioactive molecules, without being limited thereto.

In the present invention, in addition to the step of measuring the activity or expression level of the NINJ2 protein or measuring the expression level of the gene encoding the protein after treatment with the candidate substance, a step of measuring the activity or expression level of at least one of CD44 and periostin proteins or measuring the expression level of a gene encoding at least one protein may additionally be performed.

In the present invention, an agent for measuring the activity or expression level of the protein is not particularly limited. However, for example, the agent may comprise at least one selected from the group consisting of an antibody, an oligopeptide, a ligand, a peptide nucleic acid (PNA), and an aptamer, which bind specifically to the protein.

In the present invention, examples of methods for measurement or comparative analysis of the activity or expression level of the protein include, but are not limited to, protein chip assay, immunoassay, ligand binding assay, MALDI-TOF (Matrix Assisted Laser Desorption/Ionization Time of Flight Mass Spectrometry) assay, SELDI-TOF (Surface Enhanced Laser Desorption/Ionization Time of Flight Mass Spectrometry) assay, radioimmunoassay, radioimmunodiffusion, Ouchterlony immunodiffusion, rocket immunoelectrophoresis, immunohistochemical staining, complement fixation assay, two-dimensional electrophoresis assay, liquid chromatography-mass spectrometry (LC-MS), LC-MS/MS (liquid chromatography-mass spectrometry/mass spectrometry), Western blotting, and ELISA (enzyme-linked immunosorbent assay).

In the present invention, an agent for measuring the expression level of the gene encoding the protein may comprise at least one selected from the group consisting of a primer, a probe, and an antisense nucleotide, which bind specifically to the gene.

Information on the protein according to the present invention or the gene encoding the protein is known. Thus, based on this information, those skilled in the art can easily design a primer, a probe or an antisense nucleotide, which specifically binds to the gene encoding the protein.

In the present invention, examples of a method for analyzing the presence or absence and expression level of the gene include, but are not limited to, reverse transcription-polymerase chain reaction (RT-PCR), competitive RT-PCR, real-time RT-PCR, RNase protection assay (RPA), Northern blotting, and DNA chip assay.

The method of the present invention may further comprise a step of determining that the candidate substance is a drug for overcoming or treating anticancer drug resistance or a drug for enhancing anticancer drug sensitivity, when the measured activity or expression level of the NINJ2 protein or the measured expression level of the gene encoding the protein in the cancer cells or the cancer organoid decreases after treatment with the candidate substance.

In addition, the method of the present invention may further comprise a step of determining that the candidate substance is a drug for overcoming or treating anticancer drug resistance or a drug for enhancing anticancer drug sensitivity, when the activity or expression level of at least one of CD44 and periostin proteins or the expression level of the gene encoding at least one protein decreases after treatment with the candidate substance, in addition to when the measured activity or expression level of the NINJ2 protein or the measured expression level of the gene encoding the protein in the cancer cells or the cancer organoid decreases after treatment with the candidate substance.

In the present invention, the anticancer drug may be a drug comprising at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, and carmustine. Preferably, the anticancer drug may be a drug comprising at least one selected from the group consisting of epirubicin, cisplatin and 5-fluorouracil, and more preferably, may be a combination of ECF comprising epirubicin, cisplatin and 5-fluorouracil. In addition, the anticancer drug is not limited thereto and may comprise any drug belonging to the same family as ECF.

In the present invention, the cancer may be thyroid cancer, parathyroid cancer, gastric cancer, ovarian cancer, colorectal cancer, pancreatic cancer, liver cancer, breast cancer, cervical cancer, lung cancer, non-small cell lung cancer, prostate cancer, gallbladder cancer, biliary tract cancer, non-Hodgkin's lymphoma, Hodgkin's lymphoma, blood cancer, bladder cancer, kidney cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureter cancer, renal cell carcinoma, renal pelvic carcinoma, CNS central nervous system tumor, primary CNS lymphoma, spinal cord tumor, brainstem glioma, or pituitary adenoma. However, the cancer is not limited thereto and may be any type of cancer in which cancer progression, such as tumor differentiation and/or proliferation, is dependent on cancer cells and/or cancer stem cells as described in the present invention.

In the screening method according to the present invention, the recombinant vector and introduction thereof are the same as described above with respect to the anticancer drug-resistant cancer organoid, and thus detailed description thereof will be omitted in order to avoid excessive complexity of the present specification.

Advantageous Effects

When the present invention is used, it is possible to diagnose resistance to anticancer drugs such as epirubicin, cisplatin and 5-fluorouracil, which are used for anticancer therapy. Thus, upon future establishment of a treatment plan for a cancer patient, a clinician may predict the suitability of use of the above anticancer drugs before drug administration, so that an appropriate alternative anticancer drug may be used. Accordingly, it is expected that it will be possible to reduce the physical, mental and financial burdens of the patient, and ultimately, it will be possible to further improve the effect of treating cancer in the patient.

In addition, when the present invention is used, it is possible to overcome resistance to the anticancer drugs, and furthermore, effectively prevent, ameliorate or treat anticancer agent-resistant cancer.

BEST MODE

One embodiment of the present invention is directed to a composition for diagnosing anticancer drug resistance, the composition containing an agent for measuring the expression level of NINJ2 (nerve injury-induced protein 2; Ninjurin 2) protein or a gene encoding the protein.

Another embodiment of the present invention is directed to a kit for diagnosing anticancer drug resistance, the kit comprising the composition for diagnosing anticancer drug resistance according to the present invention.

Still another embodiment of the present invention is directed to a method for providing information for diagnosing anticancer drug resistance, the method comprising a step of measuring the expression level of the NINJ2 protein or a gene encoding the protein in a biological sample isolated from a subject of interest.

Yet another embodiment of the present invention is directed to a pharmaceutical composition for treating anticancer drug resistance or enhancing anticancer drug sensitivity, the pharmaceutical composition containing, as an active ingredient, an agent for reducing the activity or expression level of NINJ2 protein or an agent for reducing the expression level of a gene encoding the protein.

Still yet another embodiment of the present invention is directed to a method for treating anticancer drug resistance or enhancing anticancer drug sensitivity, the method comprising a step of administering, to a subject in need thereof, an effective amount of either an agent for reducing the activity or expression level of NINJ2 (nerve injury-induced protein 2; Ninjurin 2) protein or an agent for reducing the expression level of a gene encoding the protein.

A further embodiment of the present invention is directed to a pharmaceutical composition for preventing or treating cancer, the pharmaceutical composition containing, as an active ingredient, an agent for reducing the activity or expression level of NINJ2 protein, or an agent for reducing the expression level of a gene encoding the protein.

Another further embodiment of the present invention is directed to a method for preventing or treating cancer, the method comprising a step of administering, to a subject in need thereof, an effective amount of either an agent for reducing the activity or expression level of NINJ2 (nerve injury-induced protein 2; Ninjurin 2) protein or an agent for reducing the expression level of a gene encoding the protein.

Still another further embodiment of the present invention is directed to a method for preventing or treating cancer, the method comprising a step of administering, to a subject in need thereof, an effective amount of any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6.

Yet another further embodiment of the present invention is directed to a pharmaceutical composition for preventing or treating anticancer drug-resistant cancer, the pharmaceutical composition containing, as an active ingredient, an agent for reducing the activity or expression level of NINJ2 protein or an agent for reducing the expression level of a gene encoding the protein.

Still yet another further embodiment of the present invention is directed to a method for preventing or treating anticancer drug-resistant cancer, the method comprising a step of administering, to a subject in need thereof, an effective amount of either an agent for reducing the activity or expression level of NINJ2 (nerve injury-induced protein 2; Ninjurin 2) protein or an agent for reducing the expression level of a gene encoding the protein.

A still further embodiment of the present invention is directed to a method for preventing or treating anticancer drug-resistant cancer, the method comprising a step of administering, to a subject in need thereof, an effective amount of any one or more selected from the group consisting of an antisense nucleotide, a short interfering RNA (siRNA), a short hairpin RNA, and ribozyme, which bind complementarily to a polynucleotide consisting of the nucleotide sequence shown in SEQ ID NO: 5 or 6.

Yet still further embodiment of the present invention is directed to an anticancer drug-resistant cancer organoid comprising cancer cells expressing NINJ2 protein or a gene encoding the protein.

Another embodiment of the present invention is directed to a method for screening a drug for overcoming or treating anticancer drug resistance or a drug for enhancing anticancer drug sensitivity, the method comprising steps of: treating either cancer cells expressing NINJ2 protein or a gene encoding the protein, or a cancer organoid provided by the present invention, with a candidate substance in vitro; and measuring the activity or expression level of the NINJ2 protein or measuring the expression level of the gene encoding the protein, in the cancer cells or the cancer organoid after treatment with the candidate substance.

MODE FOR INVENTION

Hereinafter, the present invention will be described in more detail with reference to examples. These examples are only for illustrating the present invention in more detail, and it will be apparent to those of ordinary skill in the art that the scope of the present invention according to the subject matter of the present invention is not limited by these examples.

Example 1: Preparation of Cells Resistant to Anticancer Drugs (Epirubicin, Cisplatin and 5-Fluorouracil; ECF)

Figures 1B, 1C:
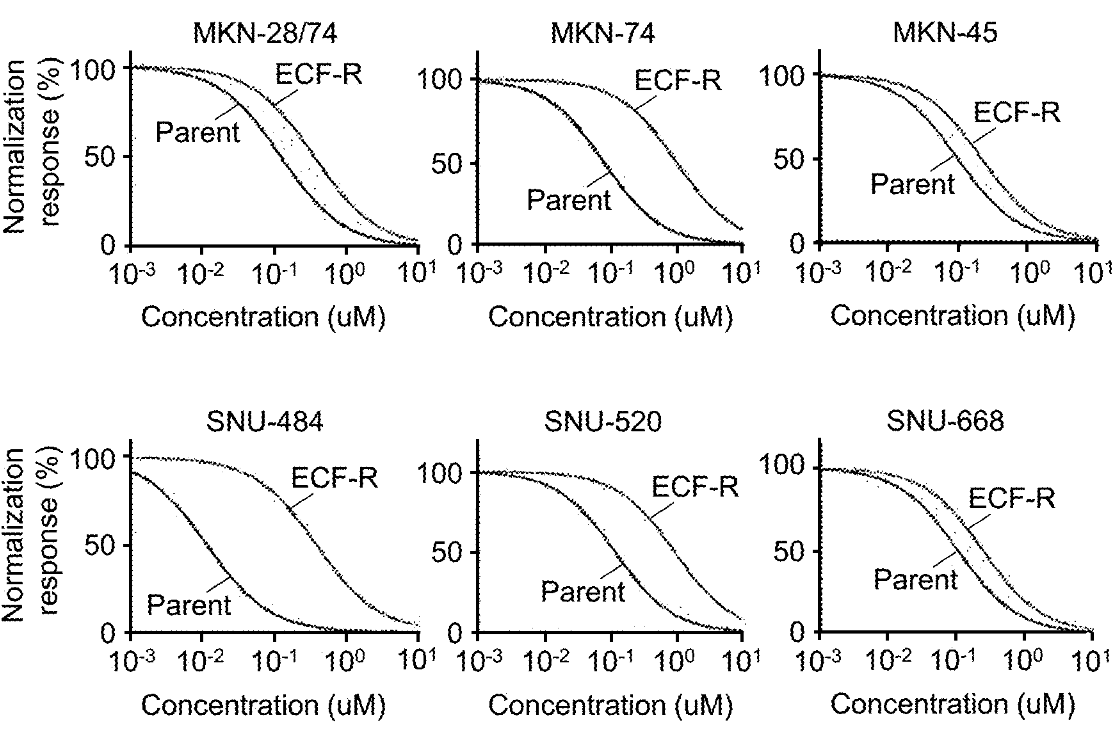
FIG. 1B shows representative $IC_{50}$ values for non-ECF-resistant parental cells and ECF-resistant cells according to one example of the present invention.
FIG. 1C shows representative $IC_{50}$ values for non-ECF-resistant parental cells and ECF-resistant cells according to one example of the present invention.
Figure 1D:
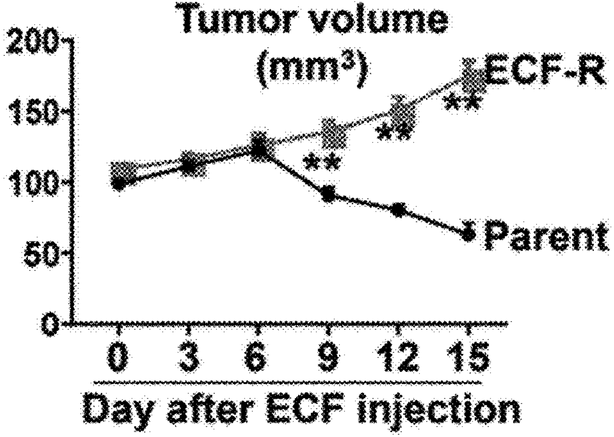
FIG. 1D shows the results of examining changes in tumor volume after injecting ECF into tumor mouse models xenografted with non-ECF-resistant parental cells and ECF-resistant cells (ECF-R), respectively, according to one example of the present invention.

To obtain gastric cancer cells resistant to an ECF combination comprising Epirubicin, Cisplatin and 5-Fluorouracil (ECF), primary human gastric cancer cell lines (SNU-488 and SNU-520) and metastatic human gastric cancer cell lines (MKN-28/74, MKN-74, MKN-45, and SNU-668) were first prepared. Thereafter, as shown in FIGS. 1A-1D, each of the gastric cancer cell lines was treated sequentially with ECF $IC_{50}$, ECF $IC_{70}$ and ECF $IC_{80}$, and then given a schedule of drug-on (3 days) and drug-off (1 to 3 weeks) for a long period of more than 2 months. To determine whether ECF-resistant gastric cancer cell lines were created, drug responsiveness was evaluated in vitro and in xenograft animal models. As a result, it could be confirmed that the $IC_{50}$ values for ECF-resistant gastric cancer cell lines significantly increased in the primary and metastatic gastric cancer cell lines compared to the parental cells (FIGS. 1B and 1C). In the case of the xenograft animal models, it could be confirmed that the volume of the tumor derived from the ECF-resistant gastric cancer cell line increased gradually, but the tumor volume decreased in the control group (FIG. 1D).

Example 2: Selection of Gene Resistant to Anticancer Drugs (Epirubicin, Cisplatin and 5-Fluorouracil; ECF) and Validation of the Potential of NINJ2 Biomarker to Diagnose ECF Resistance 2.1. Selection of NINJ2 (Nerve Injury-Induced Protein 2; Ninjurin 2)

Figure 2:
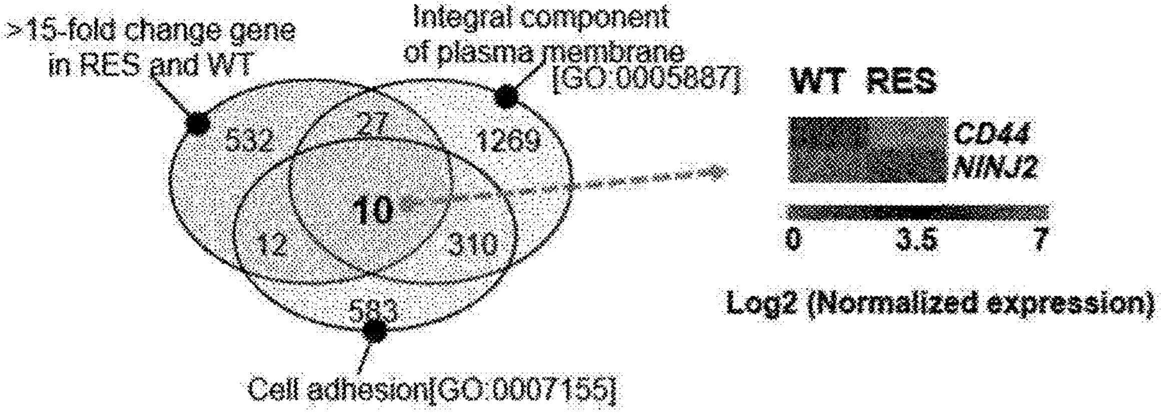
FIG. 2 shows a process of selecting genes, which commonly appear in ECF-resistant cell lines, using a heatmap according to one example of the present invention.

ECF-resistant gastric cancer cells were obtained from Example 1, and a heatmap was used to select genes commonly appearing in ECF-resistant cell lines compared to wild-type cells (see FIG. 2). For a novel gene involved in ECF drug resistance, mRNA was extracted by a protocol performed in a conventional procedure, and then mRNA expression was measured using the affymetrix HG-U133A, HG-U133 Plus 2.0 and HG-U133A 2.0 platforms. The measured gene expression was set to one gene expression value, and then a correlation analysis procedure was further performed and the results were assessed by transcriptome analysis using RNA sequencing. The present inventors could finally select a biomarker of NINJ2 (nerve injury-induced protein 2; Ninjurin 2) by focusing on changed genes in RES and WT (wild type) related to integral component of plasma membrane and cell adhesion protein. Referring to the heatmap results, it was confirmed that the gene of NINJ2 was highly expressed in the RES cell line, like CD44 which is an already known stem cell marker, and showed the same trend as CD44 (see FIG. 2). By using the marker, it is possible to select only the RES cell line, that is, cells resistant to the drugs.

Figure 3A:
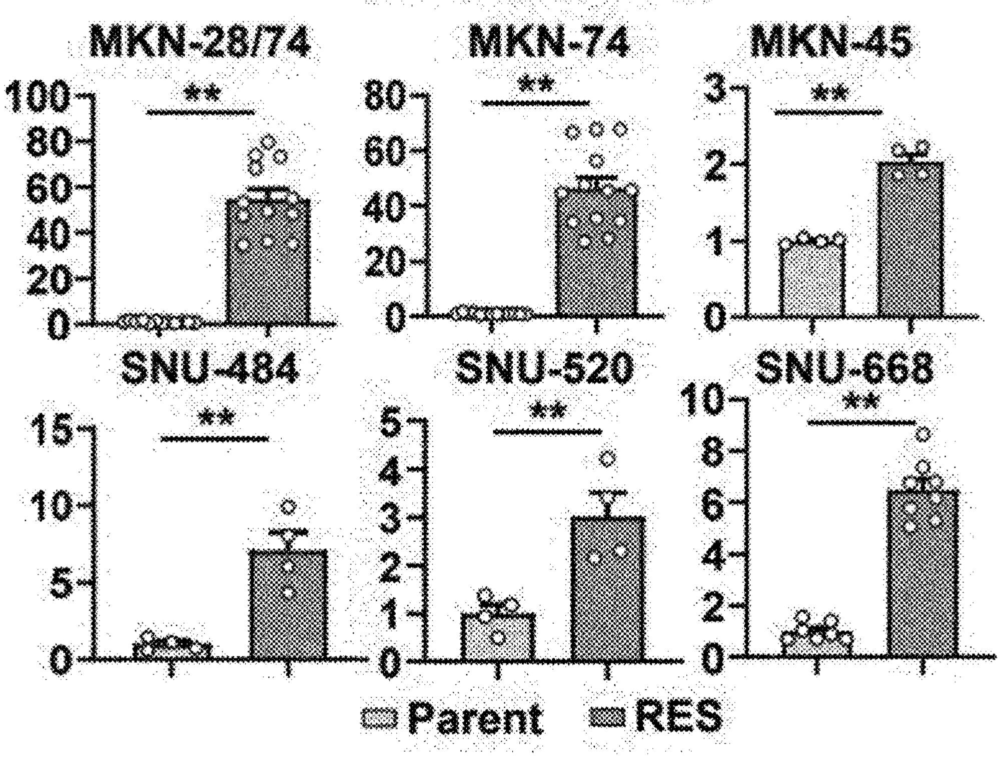
FIG. 3A shows the results of quantitative qRT-PCR analysis of the expression levels of NINJ2 proteins in non-ECF-resistant parental cells and ECF-resistant cells (ECF-R) according to one example of the present invention.
Figure 3B:
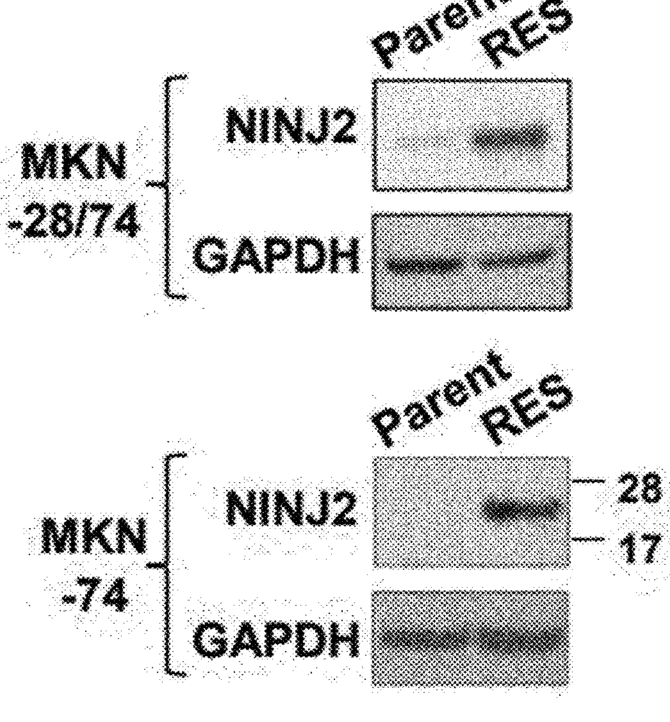
FIG. 3B shows the results of Western blot analysis of the expression levels of NINJ2 proteins in non-ECF-resistant parental cells and ECF-resistant cells (ECF-R) according to one example of the present invention.

2.2. Validation of the Potential of NINJ2 Marker to Diagnose Anticancer Drug (ECF) Resistance In order to verify whether the NINJ2 marker among the selected markers can diagnose anticancer drug (ECF) resistance, additional experiments were conducted at the cellular level and tissue level. First, the expression levels of NINJ2 mRNA and protein in ECF-resistant primary gastric cancer cell lines (SNU-488 and SNU-520) and metastatic gastric cancer cell lines (MKN-28/74, MKN-74, MKN-45, and SNU-668) were determined by qRT-PCR and Western blot analysis. As a result, as shown in FIGS. 3A and 3B, it could be confirmed that the expression levels of NINJ2 mRNA and protein were significantly higher in the ECF-resistant gastric cancer cell lines than in the parental cells.

Figure 4A:
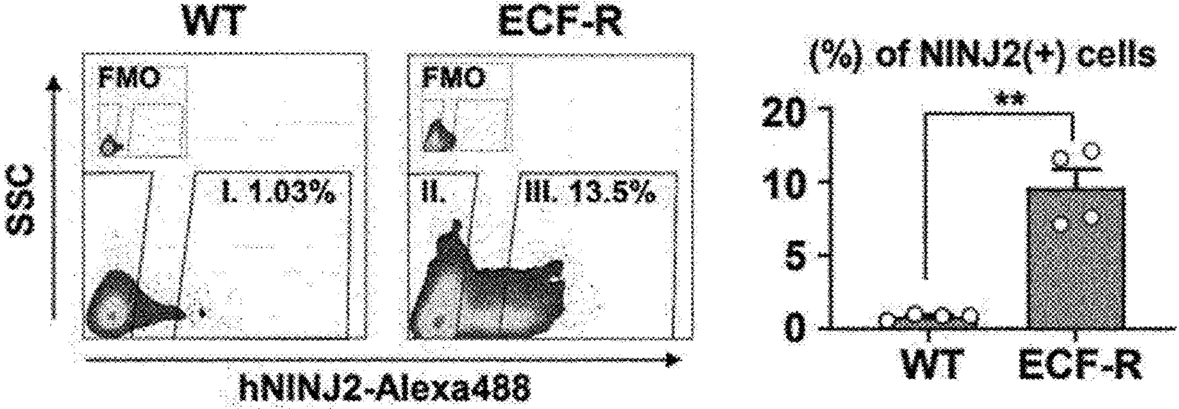
FIG. 4A shows the results of FACS performed to analyze the surface expression of NINJ2 on the wild-type cells and ECF-resistant cells (ECF-R) derived from the MKN-74 cell line, according to one example of the present invention.
Figure 4B:
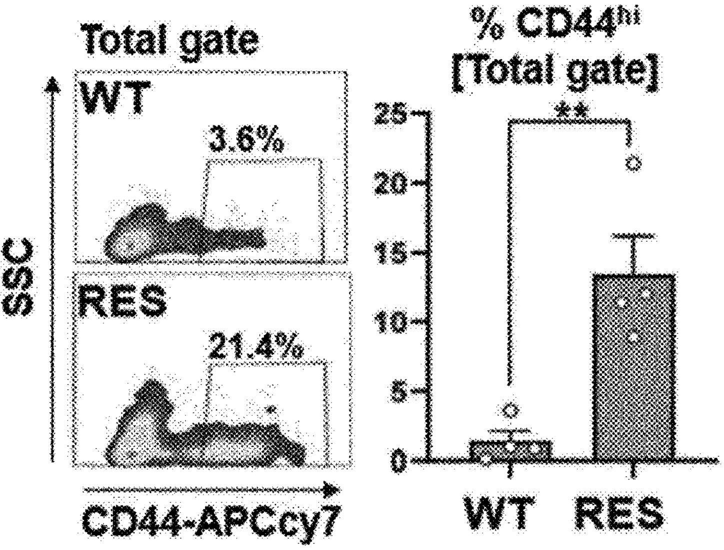
FIG. 4B shows the results of FACS performed to analyze the surface expression of CD44 on the wild-type cells and ECF-resistant cells (ECF-R) derived from the MKN-74 cell line, according to one example of the present invention.
Figure 4C:
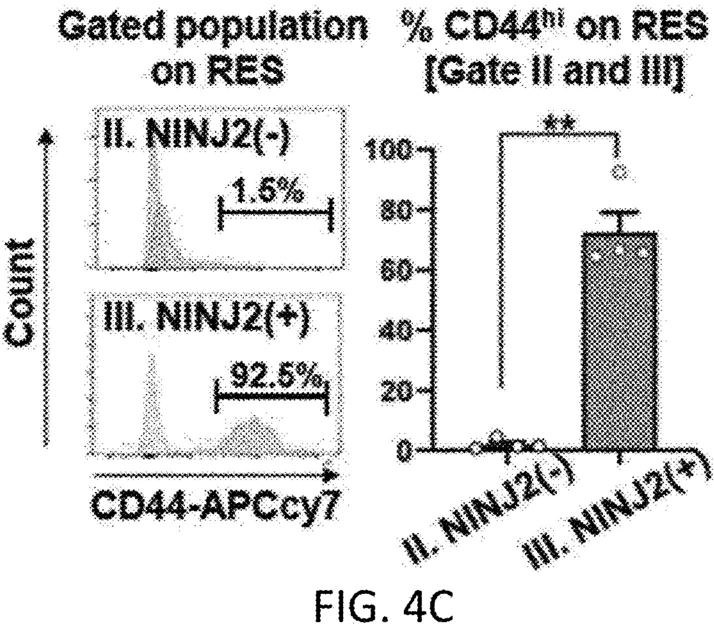
FIG. 4C shows the results of FACS performed to analyze CD44 expression on gate NINJ2 (−) and NINJ2 (+) populations in the ECF-resistant cells (ECF-R) derived from the MKN-74 cell line, according to one example of the present invention.
Figure 4D:
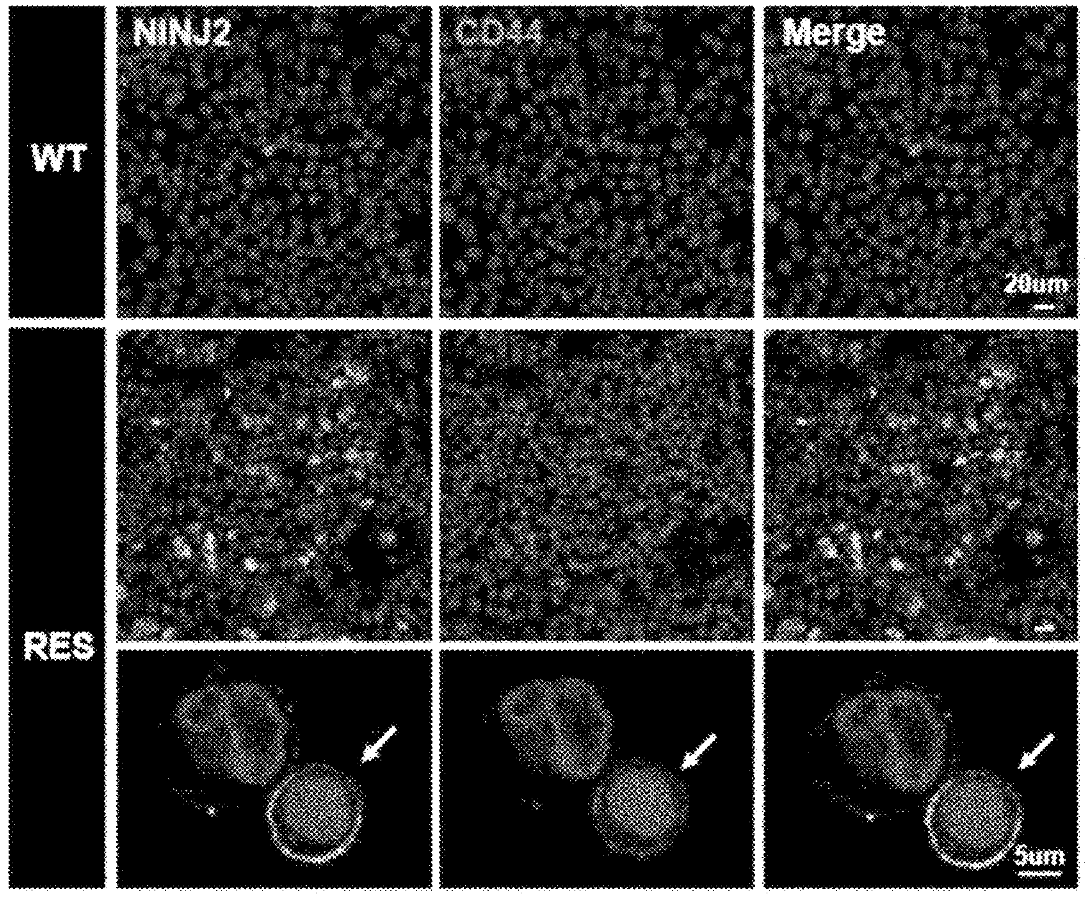
FIG. 4D depicts immunofluorescence images showing the expression level of each of markers (CD44 and NINJ2) in the wild-type cells and ECF-resistant cells (ECF-R) derived from the MKN-74 cell line, according to one example of the present invention.

Example 3: Correlation Between NINJ2 and CD44 Markers in ECF-Resistant Gastric Cancer Cell Lines In gastric cancer initiating cells, CD133, CD44, aldehyde dehydrogenase 1 (ALDH1), and ATP-binding cassette subfamily G member 2 (ABCG2) were expressed. It is well known that, in the case of cancer stem cells, the effect of anticancer therapy is lower and the risk of recurrence is also higher than in the case of conventional cancer cells. CD44 is also one of the markers expressed in cancer stem cells, and it was confirmed that the expression level of the CD44 marker was high in the ECF-resistant cell lines in which NINJ2 was highly expressed (see FIGS. 4B and 4C). Also, among ECF-resistant MKN-74 cells, the proportion of surface NINJ2-positive cells was 9.6%+1.3%, but the proportion of parental cells was 0.8%+0.09%, and among ECF-resistant MKN-74 cells, the proportion of surface NINJ2 protein-expressing cells was 13.4%+2.7%, but the proportion of parental cells was only 1.4%+0.7% (FIGS. 4A and 4B). To analyze the correlation between NINJ2 and CD44, the expression level of CD44 in NINJ2 (+) or (−) cells among ECF-resistant cells was analyzed. As a result, as shown in FIGS. 4C and 4D, it could be confirmed that, among ECF-resistant cells, the NINJ2 (+) cell population was composed mostly of CD44 high-expressing cells, whereas the NINJ2 (−) cell population was composed mostly of CD44 (−) cells. Thereby, it could be confirmed that the NINJ2 (+) CD44 hi gastric cancer-initiating cells significantly increased in the ECF-resistant gastric cancer cells.

Figure 4E:
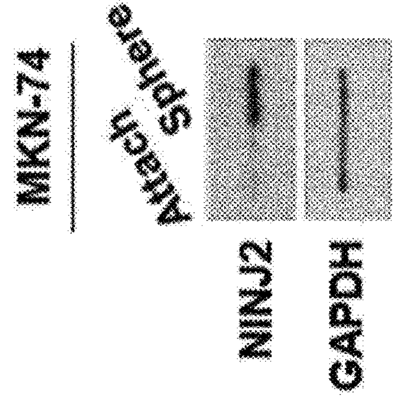
FIG. 4E shows Western blot analysis results indicating the expression level of each of markers (CD44 and hNINJ2) in tumor spheres derived from the MKN-74 cell line, according to one example of the present invention.
Figure 4E:
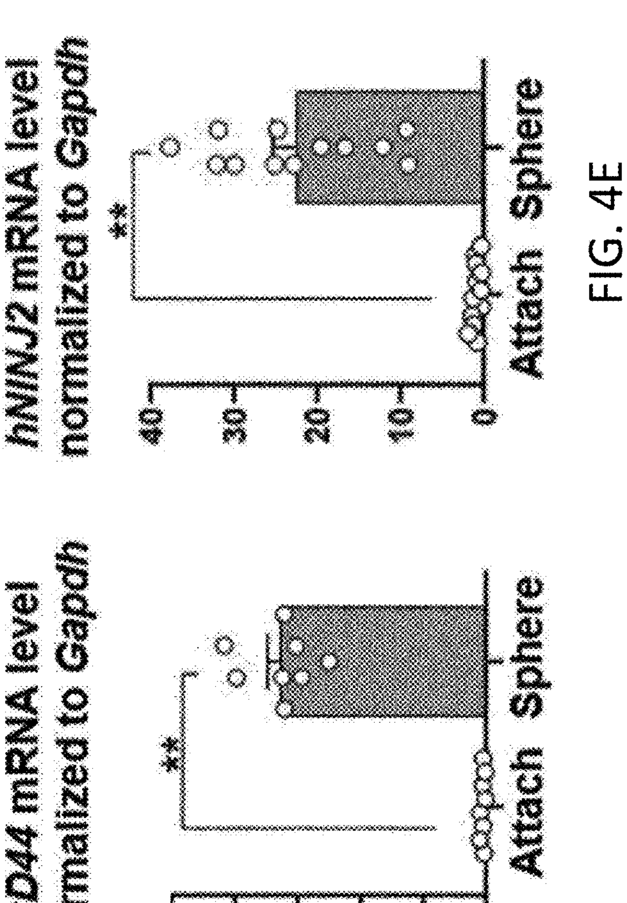
Figure 4F:
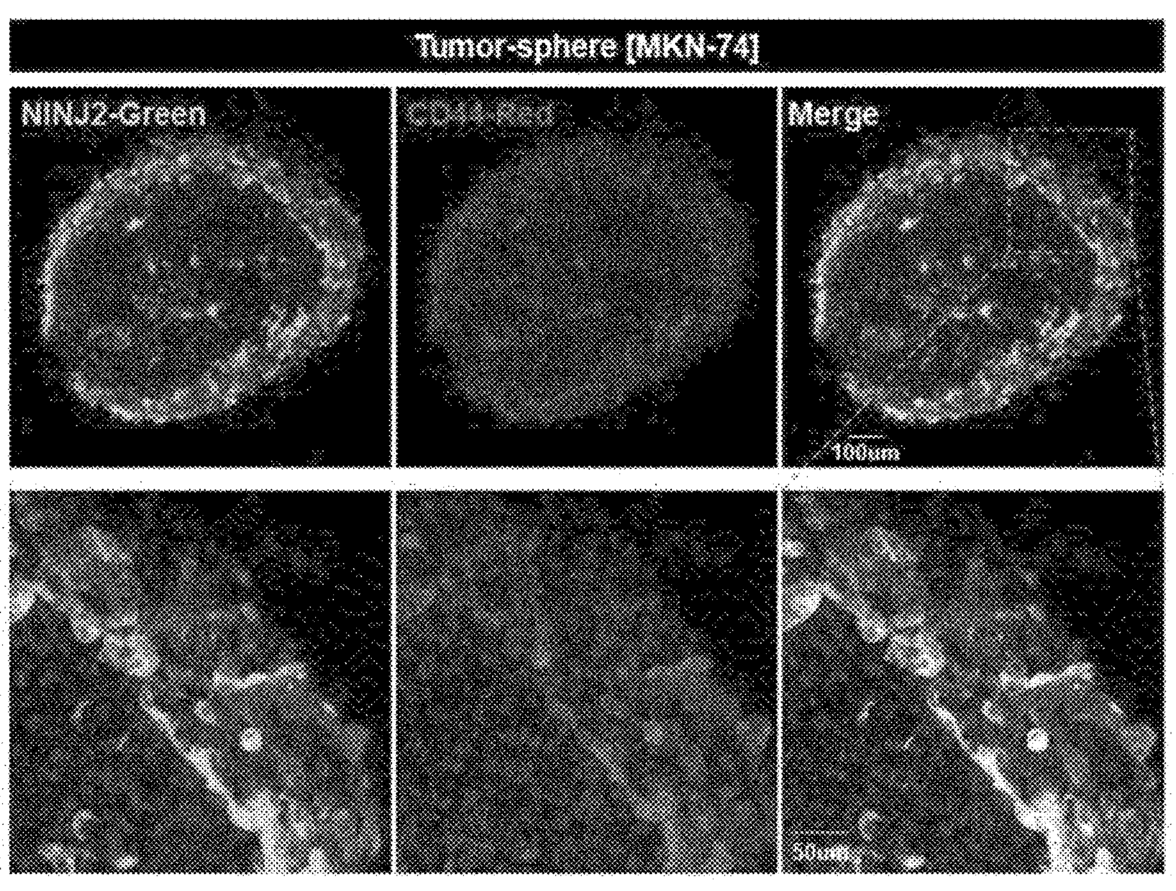
FIG. 4F depicts immunofluorescence images showing the expression level of each of markers (CD44 and hNINJ2) in tumor spheres derived from the MKN-74 cell line, according to one example of the present invention.

Next, in order to evaluate NINJ2 expression in cancer stem cells known as an anticancer drug-resistant population, cancer spheroids were prepared by culturing the MKN-74 cell line in a serum-free culture medium supplemented with growth factors. As a result of measuring CD44 and NINJ2 mRNA expression levels in the MKN-74-derived tumor spheres by qRT-PCR and analyzing the expression level of NINJ2 protein by Western blot analysis, as shown in FIG. 4E, it was confirmed that, in the MKN-74-derived tumor spheres, CD44 and NINJ2 mRNA expression levels and NINJ2 protein expression levels significantly increased. In addition, the cultured spheroids were placed on a slide, and the cells were fixed with 1% (w/v) paraformaldehyde (PFA), incubated for 30 minutes, and washed three times with PBS. The cells were incubated with a blocking buffer (BSA 1%, Triton X-100 0.05%) for 30 minutes. The cells were treated with NINJ2 antibody (R&D Systems) and incubated at 4° C. for 16 hours. The cells were washed three times with PBS. Alexa-488-tagged secondary antibody (Thermo Fisher Scientific) was added to the cells, followed by incubation for 1 hour. The cells were washed three times with PBS, treated with CD44 antibody, incubated at 4° C. for 16 hours, and then washed three times with PBS for 20 minutes. Alexa-555-tagged secondary antibody (Thermo Fisher Scientific) was added to the cells, followed by incubation for 1 hour. The cells were washed three times with PBS for 20 minutes and stained with DAPI, and then immunofluorescence images thereof were observed using a confocal microscope. As a result of examining the immunofluorescence image, as shown in FIG. 4F, it was confirmed that NINJ2 and CD44 were co-localized in the spheroid and that NINJ2 (+) CD44 hi gastric cancer-initiating cells were located on the outside of the spheroid. Thereby, it could be seen that the NINJ2 (+) cell population among ECF-resistant gastric cancer cells mainly corresponded to CD44 high-expressing gastric cancer initiating cells.

Figure 5A:
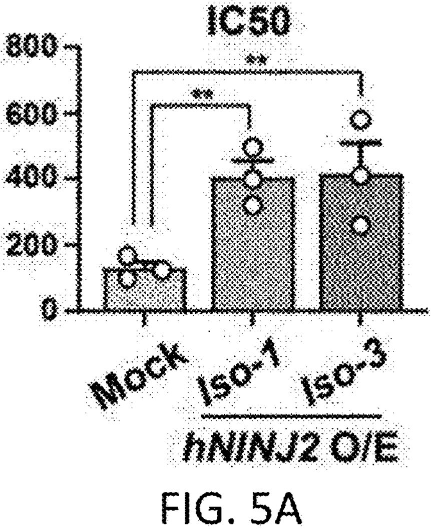
FIG. 5A shows representative $IC_{50}$ values for NINJ2 Iso-1 and Iso-3 overexpressing MKN-74 cell lines after ECF treatment according to one example of the present invention.
Figure 5B:
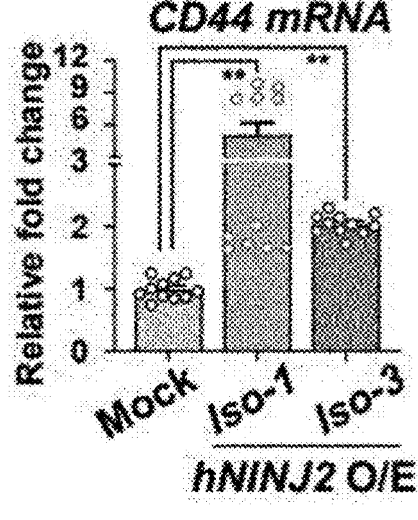
FIG. 5B shows the results of qRT-PCR performed to analyze the expression levels of CD44 mRNA in NINJ2 Iso-1 and Iso-3 overexpressing MKN-74 cell lines according to one example of the present invention.
Figure 5C:
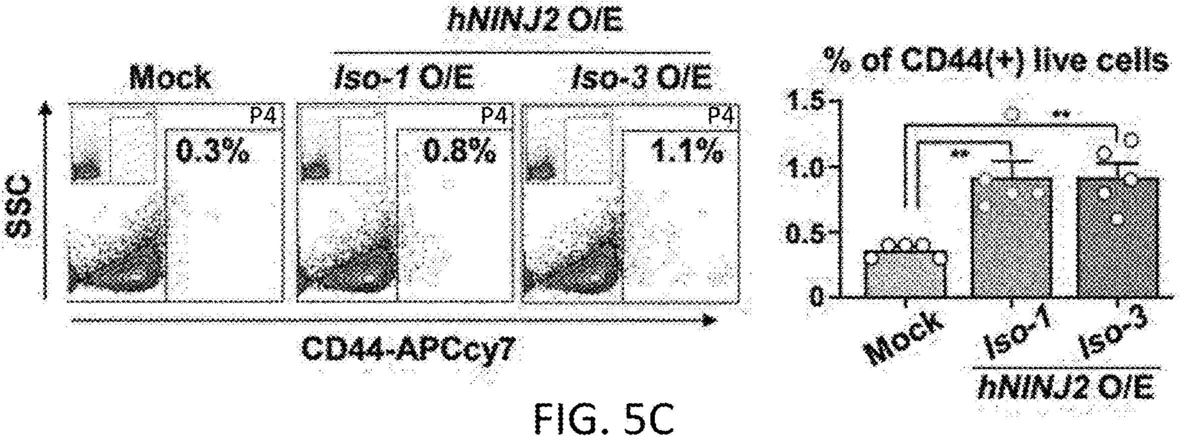
FIG. 5C shows the results of flow cytometry performed to analyze the proportion of CD44-high cells in NINJ2 Iso-1 and Iso-3 overexpressing MKN-74 cell lines according to one example of the present invention.

Example 4: Increase in Cancer Stem Cells (Cancer Initiating Cells) by NINJ2 Overexpression In order to overexpress NINJ2 in the MKN-74 cell line, NINJ2 isoform-1 (Iso-1) (NP_057617.3) and isoform-3 (Iso-3) (NP_001281275.1) were each cloned into the pHTC HaloTag® CMV-neo vectors (Promega, G7711). Thereafter, the NINJ2 Iso-1 and Iso-3 vectors were transfected into MKN-74 cells using ViaFect™ transfection reagent. Cells transfected with a growth medium containing G-418 (Promega) were selected. As a result of measuring cell viability after ECF treatment of the NINJ2 Iso-1 and Iso-3 overexpressing gastric cancer cell lines, as shown in FIG. 5A, it was confirmed that the viabilities of the NINJ2 Iso-1 and Iso-3 overexpressing gastric cancer cell lines were significantly higher than that of parental cells. In addition, it could be confirmed that the CD44 mRNA expression level and the number of CD44-expressing cells significantly increased in the NINJ2 Iso-1 and Iso-3 overexpressing gastric cancer cell lines (FIGS. 5B and 5C).

Figure 5D:
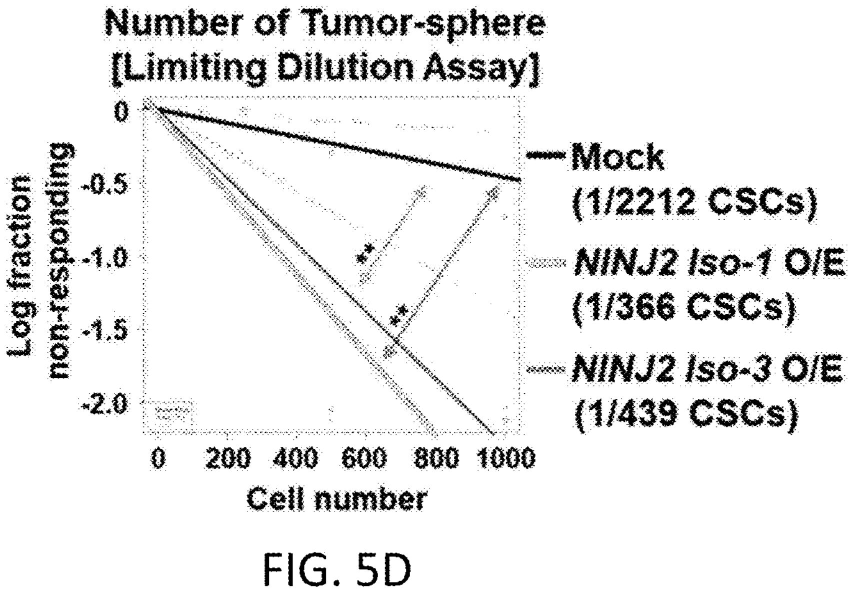
FIG. 5D shows the results of in vitro limiting dilution analysis performed on NINJ2 Iso-1 and Iso-3 overexpressing MKN-74 cell lines according to one example of the present invention.

Next, in order to examine the frequency of gastric cancer initiating cells inducing tumorigenic properties, the sphere-forming ability was evaluated by in-vitro limiting dilution analysis. More specifically, NINJ2 Iso-1 and Iso-3 overexpressing cell lines were each diluted 2-fold and dispensed in 96-well plates at a density of 1,000 to 8 cells/well. The cells were cultured in DMEM-F12 supplemented with 20 ng/ml rhEGF, 20 ng/ml rhbFGF and 5 μg/ml insulin, and quantified by extreme limiting dilution assay (ELDA). As a result, as shown in FIG. 5D, it was confirmed that gastric cancer initiating cells were abundant in the NINJ2 Iso-1 and Iso-3 overexpressing gastric cancer cells.

Figure 5E:
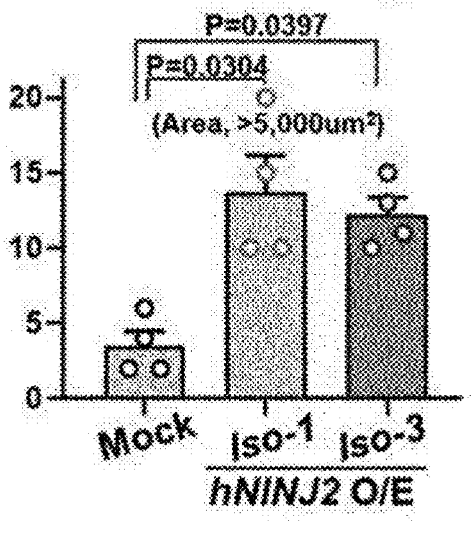
FIG. 5E shows the results of analyzing the number of tumor spheres formed from NINJ2 Iso-1 and Iso-3 overexpressing MKN-74 cell lines according to one example of the present invention.

1,000 NINJ2 Iso-1 or Iso-3 overexpressing cells were dispensed in 24-well plates, and the cells were cultured in DMEM-F12 supplemented with 20 ng/ml rhEGF, 20 ng/ml rhbFGF, and 5 μg/ml insulin in the same manner as described above. After 10 days, the number of tumor spheres was counted. In this case, only spheres measured to have a size of 5,000 μm2 or more were counted. As a result, it could be confirmed that the number of tumor spheres was increased by overexpression of NINJ2 Iso-1 and Iso-3 (see FIG. 5*e* FIG. 5E).

Example 5: Increase in Cell Cycle Arrest by NINJ2 Overexpression

Figure 6:
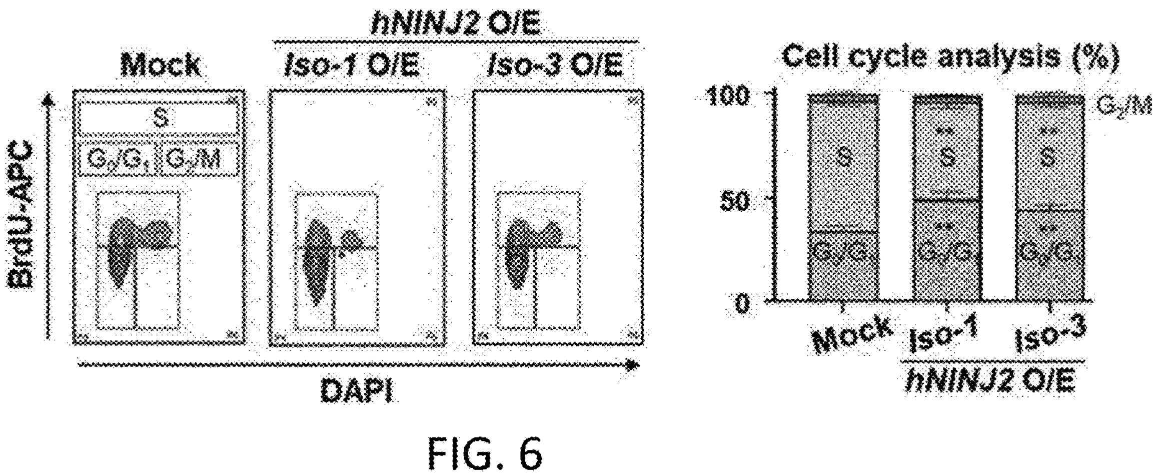
FIG. 6 shows the results of flow cytometry performed to analyze changes in cell cycle in NINJ2 Iso-1 and Iso-3 overexpressing MKN-74 cell lines according to one example of the present invention.

Cancer cells in quiescence are known as the major factor of resistance to many anticancer drugs. Accordingly, the present inventors examined an NINJ2-induced change in cell cycle. Bromodeoxyuridine (BrdU) was added to the cells overexpressing NINJ2 Iso-1 and Iso-3 from the gastric cancer cell line MKN-74, and the cells were cultured for an additional hour. After staining with anti-bromodeoxyuridine and bis-benzamide (Hoeschest 33342), the cell cycle was analyzed using a flow cytometer. As a result, it was confirmed that cell cycle arrest was significantly increased by inhibiting the progression from the G0/G1 phase to the S phase inducing anti-proliferative activity, in the NINJ2 Iso-1 and Iso-3 overexpressing gastric cancer cells (see FIG. 6).

Example 6: Identification of ECF Drug Resistance-Inducing Mechanism

Figure 7A:
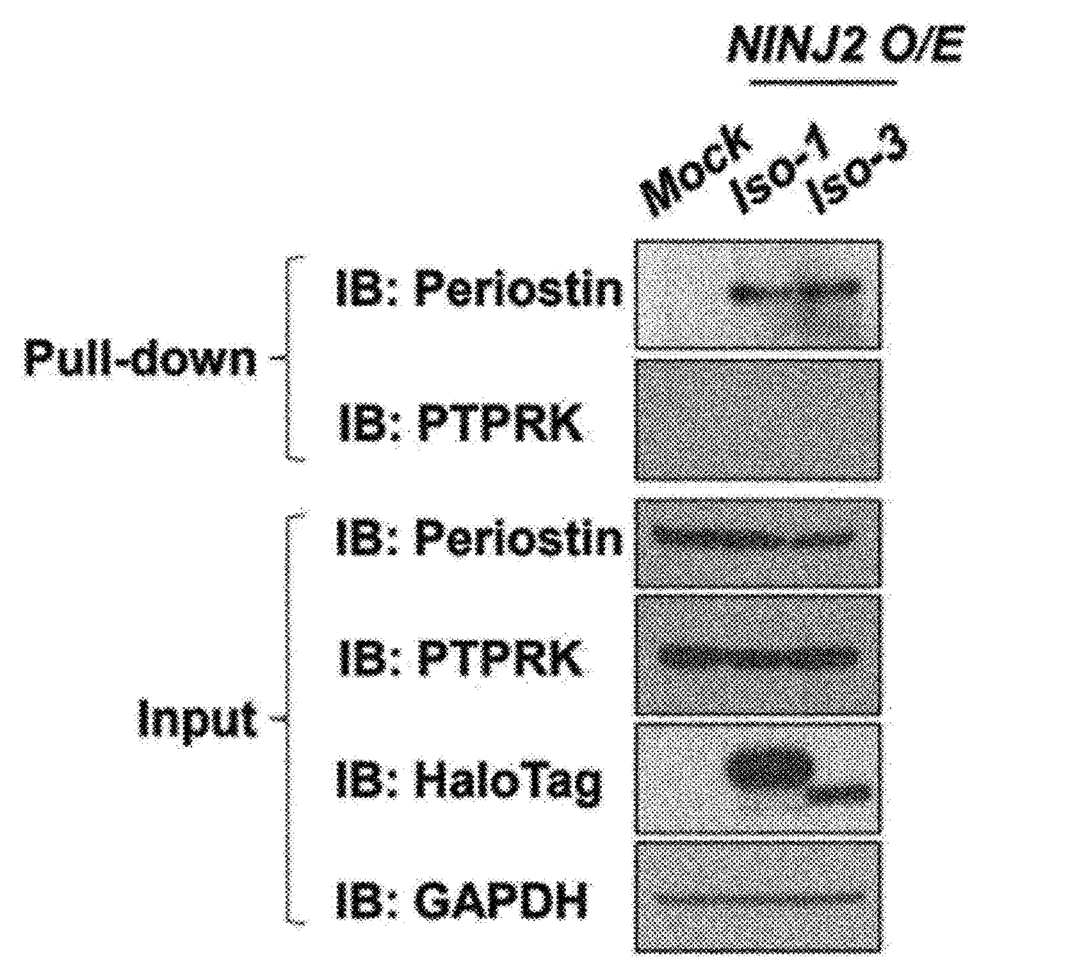
FIG. 7A shows the results of performing immunoblotting analysis (co-immunoprecipitation; co-IP) using the HaloTag pull-down system (G6504, Promega) to examine NINJ2/periostin interaction from stable NINJ2-HaloTag MKN-74 cancer cells according to one example of the present invention.
Figure 7B:
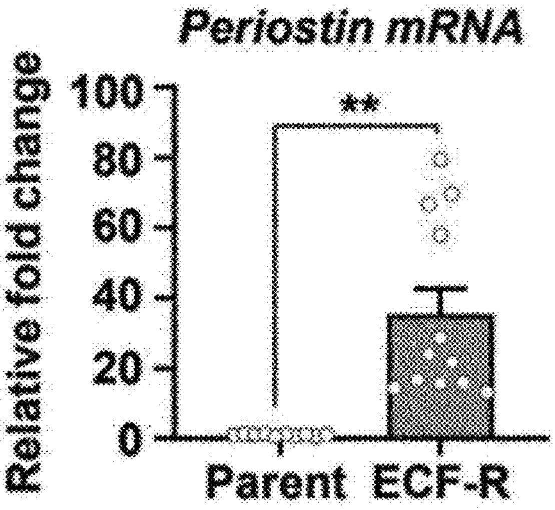
FIG. 7B shows the results of measuring the expression level of periostin mRNA by qRT-PCR after isolating mRNA from ECF-resistant MKN-74 cancer cells, according to one example of the present invention.
Figure 7C:
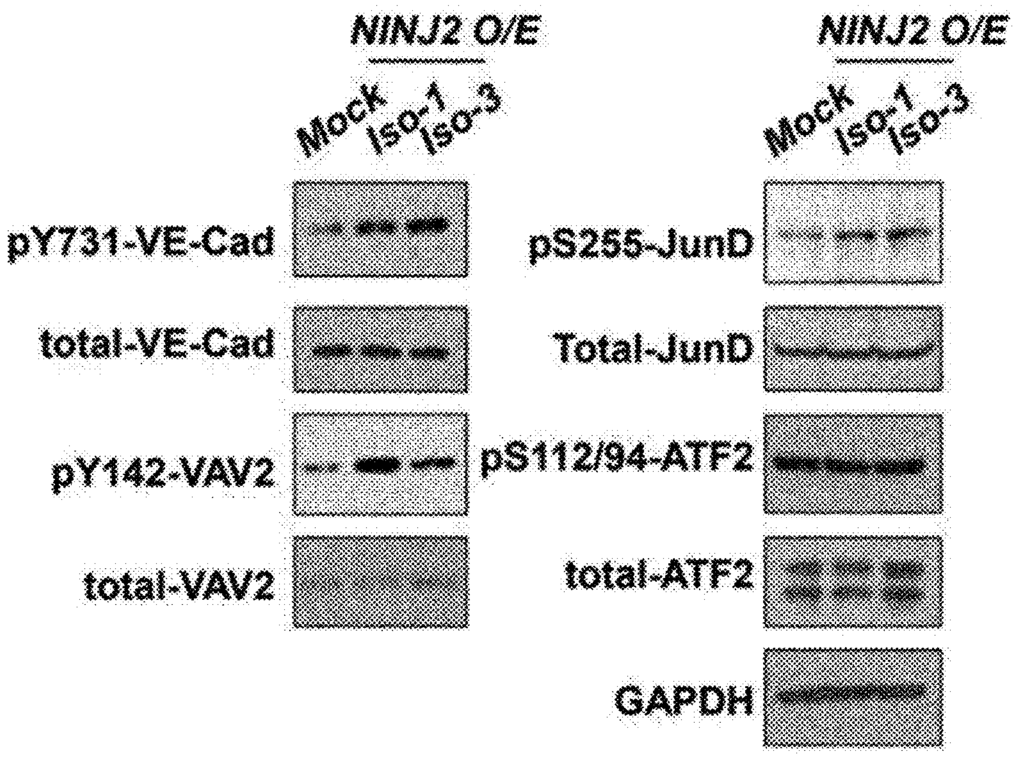
FIG. 7C shows the results of Western blotting analysis of proteins highly expressed in NINJ2 Iso-1 and Iso-3 overexpressing MKN-74 cell lines, according to one example of the present invention.

To investigate the mechanism by which NINJ2 induces drug resistance, the present inventors selected candidate proteins that interact with NINJ2. To this end, the NINJ2 complex was pulled-down using a HaloTag pull-down system (G6504, Promega) according to the manufacturer's instructions, and then analyzed by liquid chromatography-tandem mass spectrometry (LC-MS/MS). As NINJ2-interacting proteins, periostin, PTPRk (Protein Tyrosine Phosphatase Receptor Type K), RNA-binding protein 28, and fibrinogen gamma chain were identified. Among the candidate proteins, periostin and PTPRk are known to be involved in drug resistance, and only periostin is involved in induction of ECF drug resistance. It could be confirmed through immunoblotting analysis after pull-down that NINJ2 interacted with periostin to induce ECF resistance (see FIG. 7A). In addition, the expression level of periostin in the ECF-resistant MKN74 cell line was additionally measured. As a result, it could be confirmed that the expression level of periostin in the ECF-resistant cell line was as high as that of NINJ2 (see FIG. 7B). Meanwhile, as a result of performing phospho-antibody array using the NINJ2-overexpressing gastric cancer cell line, the four phosphorylated proteins VE-Cadherin (Phospho-Tyr731), VAV2 (Phospho-Tyr142), JunD (Phospho-Ser255) and ATF2 (Phospho-Ser112/94), which were up-regulated by 1.5 times or more, were identified. Consistent results were identified by Western blot analysis (see FIG. 7C). From the above results, it can be seen that NINJ2 induces ECF drug resistance in the VAV2, JunD and ATF2 pathways through VE-cadherin activation. Taking the above results together, it is suggested that not only the NINJ2 marker may be used to diagnosis ECF resistance, but also the periostin marker interacting with NINJ2 may also be additionally used.

Example 7: Evaluation of Resistance Treatment Potential of shNINJ2 Using ECF-Resistant Gastric Cancer Cell Line To evaluate whether NINJ2 is involved in drug resistance, a stable NINJ2 knockdown (K/D) ECF-resistant cancer cell line was prepared using shRNA lentiviral particles and puromycin. More specifically, for stable NINJ2 knockdown in ECF-resistant MKN-74 cells, two shRNAs (TRCN0000063773 (Clone-1) and TRCN0000063775 (Clone-2)) targeting different partial regions of NINJ2 genes (Isoform-1, Isoform-2 and Isoform-3) as shown in Table 1 below were used, and a non-targeting pLKO.1-puro shRNA control (SHC002) was used as a negative control. The shRNA clones (TRCN0000063773, TRCN0000063775 and SHC002) containing the pMDLg/pRRE, pRSV-Rev and pMD2.G plasmids, respectively, were transfected into 293T cells using Fugene HD (Promega) according to the manufacturer's instructions. After 48 hours, each supernatant was collected and filtered, and ECF-resistant MKN-74 cells were transduced with lentiviral particles and cultured in a growth medium containing puromycin. After NINJ2 knockdown in the lentivirus-transduced MKN-74 cells was confirmed using qRT-PCR, the cells were treated with ECF, and an examination was made as to whether cancer cells in the negative control (Mock) and the shNINJ2 groups (clone 1 and clone 2) re-grew.

TABLE 1

| Gene | Clone | NINJ2-targeting region sequence | Hairpin sequence |
|---|---|---|---|
| NINJ2 | TRCN0000063773 | CGTGGTCATTGCA CGGCTGAA (SEQ ID NO: 5) | 5'-CCGG- CGTGGTCATTGCACGGCTGAA- CTCGAG- TTCAGCCGTGCAATGACCACG- TTTTTG-3' (SEQ ID NO: 9) |
| NINJ2 | TRCN0000063775 | CTGAACCTGAATG AGGTAGAA (SEQ ID NO: 6) | 5'-CCGG- CTGAACCTGAATGAGGTAGAA- CTCGAG- TTCTACCTCATTCAGGTTCAG- TTTTTG-3' (SEQ ID NO: 10) |
| Control | SHC002 | — | 5'- CCGGCAACAAGATGAAGAGCACCAA CTCGAGTTGGTGCTCTTCATCTTGTTG TTTTT-3' (SEQ ID NO: 13) |

Figure 8:
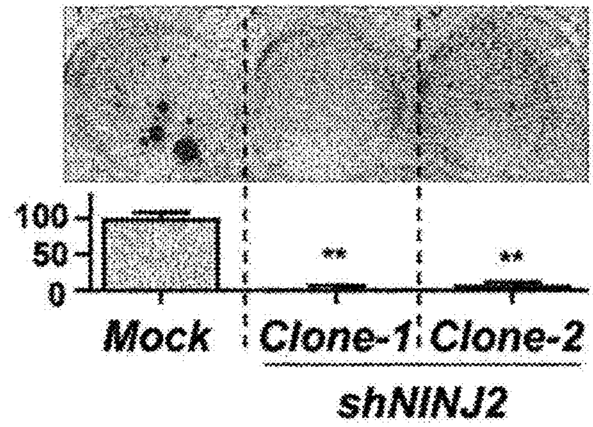
FIG. 8 shows the results of analyzing cell viability by crystal violet staining and WST-1 assay after introducing human NINJ2-targeting shRNA lentiviral particles (Clone-1 and Clone-2) into the ECF-resistant MKN-74 cell line and then administering ECF to in the cell line, according to one example of the present invention.

As shown in FIG. 8, as a result of performing crystal violet staining and WST-1 analysis 3 weeks after ECF treatment, it could be confirmed that, in the case of the NINJ2 knockdown (K/D) resistant cancer cells (clone-1 and clone-2), the recurrence and regrowth of cancer cells were significantly inhibited compared to those in the negative control (Mock). This suggests that resistance to ECF drugs is overcome upon knockdown of NINJ2 at the cellular level.

Example 8: Evaluation of Resistance Treatment Potential of siNINJ2 Using Animal Model Transplanted with ECF-Resistant Gastric Cancer Cell Line 8.1. Preparation of Animal Model Transplanted with ECF-Resistant Gastric Cancer Cell Line A mouse model was prepared by xenografting Balb/c nude mice with the spheroids prepared from the MKN-28/74 cell line by the method of Example 3. Specifically, 107 ECF-resistant cancer cells (ECF-R cancer cells) and parental cancer cells were subcutaneously injected into Balb/c nude mice, respectively, and an examination was made as to whether the animal model xenografted with the ECF-resistant cancer cells (RES) established in vitro had acquired ECF drug resistance. Thereafter, to evaluate the resistance treatment effect of NINJ2 inhibition using the prepared ECF-resistant animal model, expression of NINJ2 was inhibited using primers for siNINJ2 (represented by SEQ ID NOs: 11 and 12) and primers for a control as shown in Table 2 below, and then an additional drug administration experiment was performed. To this end, 5.7 mg/kg of epirubicin, 6.67 mg/kg of cisplatin and 22 mg/kg of 5-FU were administered intratumorally to xenograft model mice having a tumor size of 100 $mm^3$ once a week for 15 days, and the tumor weight and the tumor volume were measured every 3 days using digital calipers. As described above, the ECF administration experiment was conducted on each of a control group, an NINJ2-knockout RES cell line group and an RES cell line group highly expressing NINJ2 for about one month.

TABLE 2

| Primer | Direction | Sequence (5'→3') | SEQ ID NO |
|---|---|---|---|
| siNINJ2 | Sense | GUAAGGCAUGUCUGUCUAAGG CC | SEQ ID NO: 11 |
| | Antisense | GGCCUUAGACAGACAUGCCUU AC | SEQ ID NO: 12 |
| Control | Sense | UUCUCCGAACGUGUCACGUTT | SEQ ID NO: 14 |
| | Antisense | ACGUGACACGUUCGGAGAATT | SEQ ID NO: 15 |

8.2. Evaluation of Resistance Treatment Effect of siNINJ2

Figure 9A:
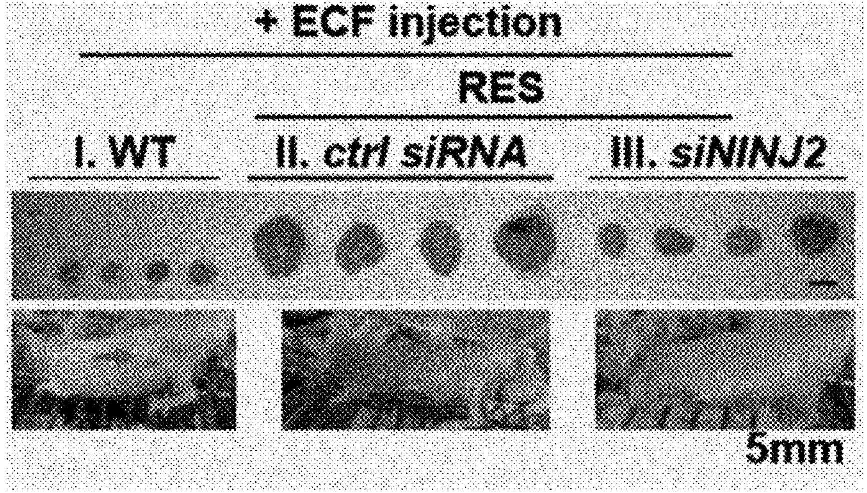
FIGS. 9A and 9B show the results of measuring changes in tumor volume and weight after transplanting wild-type or scrambled siRNA RES and siNINJ2 RES cancer cell lines from the MKN-28/74 cell line into nude mice and then administering ECF and siRNA to the nude mice when the tumor volume reached 100 $mm^3$, according to one example of the present invention.
Figure 9B:
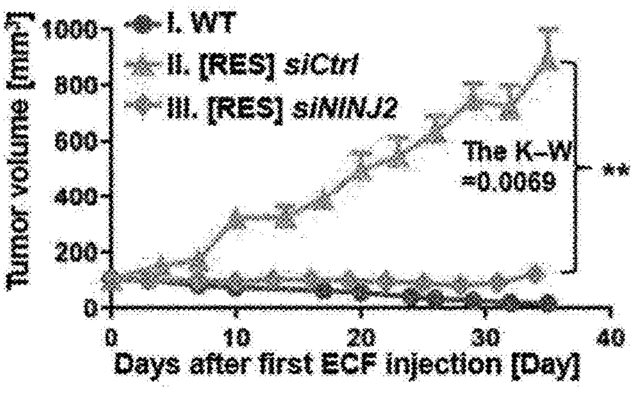

Referring to FIG. 9A, it was confirmed that the tumor volume changed after the ECF drugs were administered to the animal model xenografted with each cell line group. FIG. 9B depicts graphs showing the results of quantifying the changes in the tumor volume and weight. It could be confirmed that the tumor volume and weight significantly decreased in the NINJ2-knockout RES cell line in which the expression of NINJ2 mRNA was inhibited, compared to the RES group. A large difference in tumor volume appeared over time, suggesting that resistance to ECF drugs was overcome.

Figure 10A:
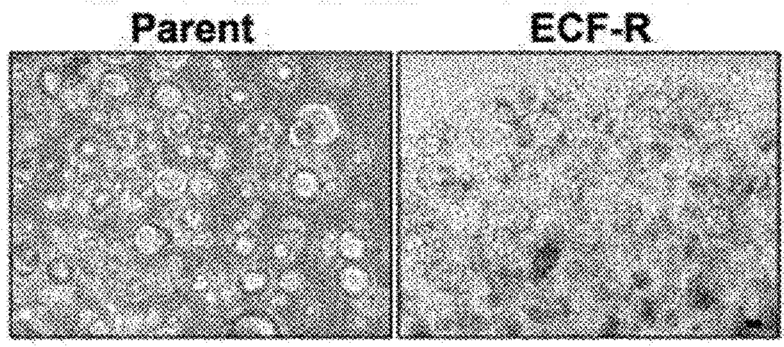
FIG. 10A shows the morphologies of a parent organoid and an ECF-resistant human gastric cancer organoid, and representative $IC_{50}$ values after ECF treatment, according to one example of the present invention.
Figure 10A:
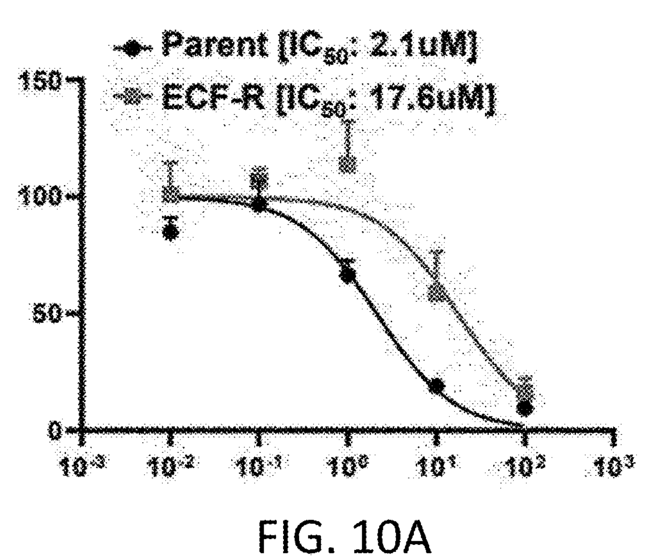
Figure 10B:
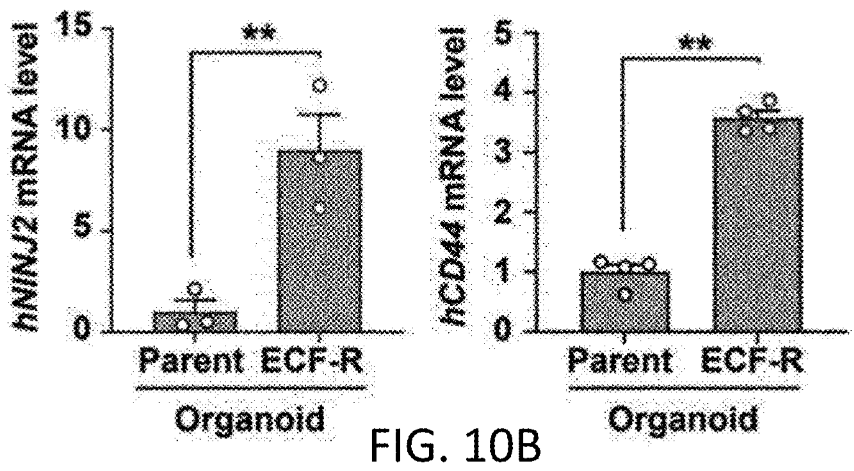
FIG. 10B shows the results of comparing the mRNA expression levels of human NINJ2 and CD44 in a parent organoid and an ECF-resistant human gastric cancer organoid, according to one example of the present invention.

Example 9: Identification of Increased Expression of NINJ2 in ECF-Resistant Gastric Cancer Organoid and Clinical Significance for Cancer Progression Patient-derived human gastric tumor organoids (HCM-BROD-0115-C16, PDM-135) were purchased from the American Type Culture Collection (ATCC), subcultured according to the ATCC guidelines, and used in the experiment. Organoids were treated with ECF at an $IC_{50}$ concentration, and after 72 hours, the medium was replaced with a drug-free medium, and two additional passages were performed. Next, the organoids were exposed to appropriate $IC_{70}$ and $IC_{80}$ concentrations, and then the above procedure was repeated. In order to prevent the organoids from reverting to the ECF drug-sensitive state, the organoids were treated with ECF at an $IC_{80}$ concentration every 3 weeks, thereby constructing ECF-resistant organoids. FIG. 10A shows microscopic observation photographs of parental gastric cancer organoids and ECF-resistant gastric cancer organoids, and shows the results of measuring $IC_{50}$ for ECF of each organoid. As a result of quantifying the expression levels of NINJ2 and CD44 mRNA in parental gastric cancer organoids and ECF-resistant gastric cancer organoids by qRT-PCR, as shown in FIG. 10B, it could be confirmed that the expression levels of NINJ2 and CD44 mRNA were significantly higher in the ECF-resistant gastric cancer organoids than in the parenteral gastric cancer organoids, like the results obtained in the cell lines.

Figure 10C:
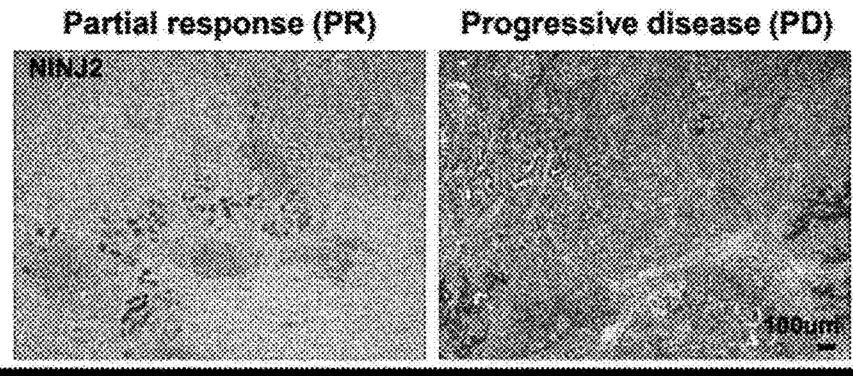
FIG. 10C shows the results of performing NINJ2 scoring analysis through histological analysis of gastric tumor patients showing partial response (PR), stable disease (SD) and progressive disease (PD), according to one example of the present invention.
Figure 10D:
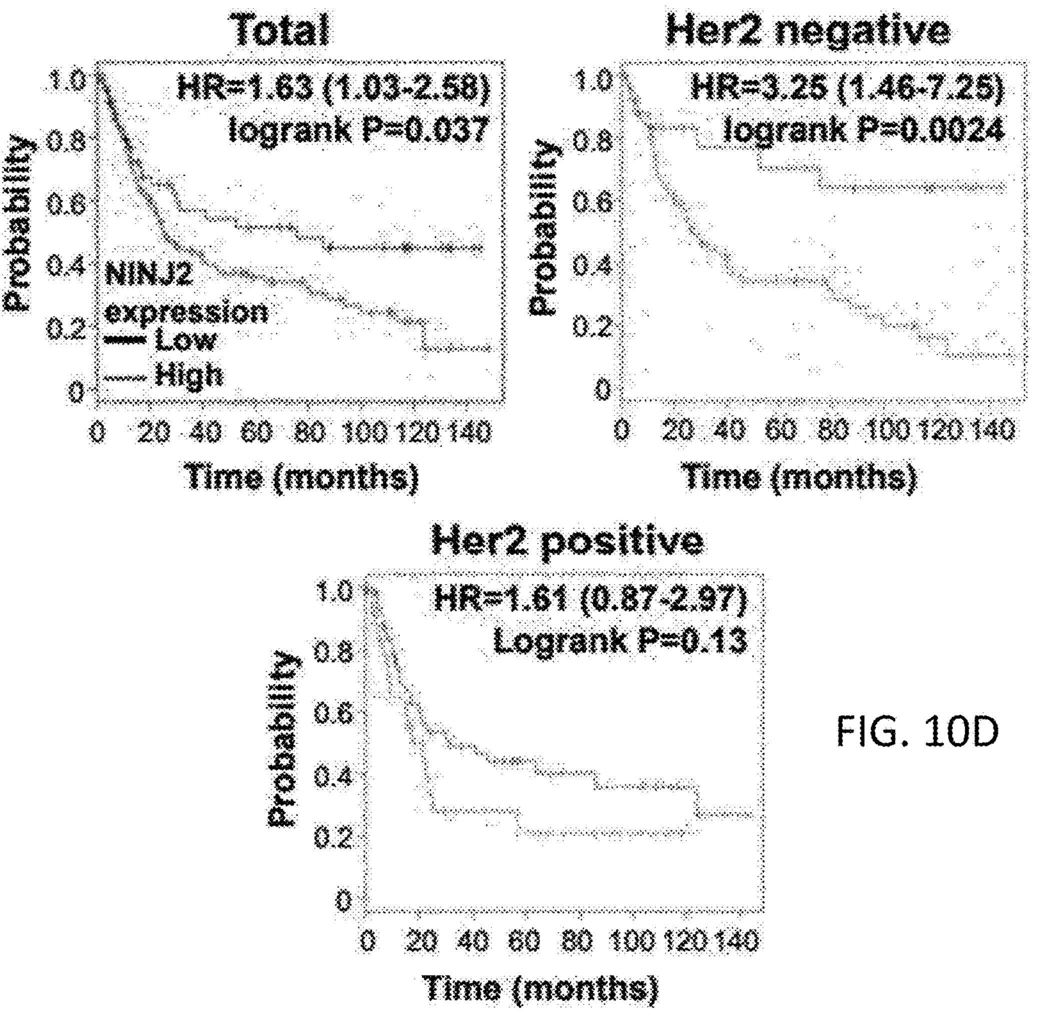
FIG. 10D shows Kaplan-Meier curves for the overall survival (OS) of gastric cancer patients, obtained through public data, according to one example of the present invention.

Next, to examine the clinical relevance between NINJ2 expression level and drug response, two pathologists analyzed the intensity and extensive expression of NINJ2 through histological analysis of gastric cancer patients showing partial response (PR), stable disease (SD) and progressive disease (PD). As a result, as shown in FIG. 10C, it was confirmed that the extensive expression of NINJ2 was significantly higher in PD than in PR/SD. Next, in order to confirm the clinical relevance between NINJ2 expression level and survival rate, Kaplan-Meier analysis and log-rank test were performed using the hazard ratio (HR) of gastric cancer patients and using public data. As a result, it could be seen that the survival rate was very low in the NINJ2-expressing group among gastric cancer patients, and in particular, it was confirmed that the NINJ2 high-expressing group in the Her2-negative group showed an increase in overall survival compared to the Her2-positive group (see FIG. 10D).

Taking the above-described results of Examples 1 to 9 together, it can be seen that it is possible to use the NINJ2 marker and the periostin marker for diagnosis of ECF resistance, and furthermore, it is possible to overcome ECF drug resistance by inhibiting the expression of NINJ2. Accordingly, it is expected that anticancer effects can be significantly improved by treating anticancer drug resistance in patients who have developed anticancer drug resistance after ECF treatment.

Although the present invention has been described in detail with reference to the specific features, it will be apparent to those skilled in the art that this detailed description is only of a preferred embodiment thereof, and does not limit the scope of the present invention. Thus, the substantial scope of the present invention will be defined by the appended claims and equivalents thereto.

INDUSTRIAL APPLICABILITY

The composition according to the present invention can not only diagnose anticancer drug resistance, but can also treat cancer very effectively. In addition, the composition may be very effectively used to overcome anticancer drug resistance, and furthermore, to effectively prevent, ameliorate or treat anticancer drug-resistant cancer.

SEQUENCE LIST FREE TEXT

```
SEQ ID NO 1:
mesarenidl qpgssdprsq pinlnhyatk ksvaesmldv alfmsnamrl

kavleqgpss hyyttlvtli slslllqvvi gvllvviarl nlnevekqwr Inqlnnaati lvfftvvinv fitafgahkt

gflaarasrn pl

SEQ ID NO 2:
mldvalfmsn amrlkavleq gpsshyyttl vtlislslll qvvigvllvv iarlnlneve

kqwrlnglnn aatilvfftv vinvfitafg ahktgflaar asrnpl

SEQ ID NO 3:
agagactcag acggcggagc ctggaggage ccacgcagtc tgttcccggc

acccggtgcg tgtgaaggga cttgagggca gcgagatgga atcagcaaga gaaaacateg accttcaacc

tggaagctcc gaccccagga gccagcccat caacctgaac cattacgcca ccaagaagag cgtggcggag

agcatgctgg acgtggccct gttcatgtcc aacgccatgc ggctgaaggc ggtgctggag cagggaccat cctctcacta

ctacaccacc ctggtcaccc tcatcagcct ctctctgctc ctgcaggtgg tcatcggtgt cctgctcgtg gtcattgcac

ggctgaacct gaatgaggta gaaaagcagt ggcgactcaa ccagctcaac aacgcagcca ccatcttggt cttcttcact
```

-continued gtggtcatca atgttttcat tacagccttc ggggcacata aaacagggtt cctggctgcc agggcctcaa ggaatcctct ctgaatgcag cctgggaccc aggttctggg cctggaactt ctgcctcctt cctccgtgat ctgccaggct cgtgggcact ttccacagcc caggagagct tctgaaagga cagtatagct gcccttgctc cctacccaca gcacctgagt taaaaagtga tttttatgtt attggtctaa gggacttcca tettggtctg aagtcctgag ctcagacgca ggtactgcca gccatacctt cctggtagca tctgctggac ctaagtaagg catgtctgtc taaggccaag tctgcccggc ttaaggatgc tggttctgac tctaccccac tgcttccttc tgctccaggc ctcaattttc ccttcttgta aaatggaatc tatatctata aaggtttctt caaatcca SEQ ID NO 4:
gttgcaaagc agccgctcgg tggccgtaca acgcttcatc tctccgagcc tcggtttcct catctccagc cctaaaatga cgacacgccc cacaggtctt gggaggatta agtgagggga catgagcctg gaagctccga ccccaggagc cagcccatca acctgaacca ttacgccacc aagaagagcg tggcggagag catgctggac gtggccctgt tcatgtccaa cgccatgcgg ctgaaggcgg tgctggagca gggaccatcc tctcactact acaccaccct ggtcaccctc atcagcctct ctctgctcct gcaggtggtc atcggtgtcc tgctcgtggt cattgcacgg ctgaacctga atgaggtaga aaagcagtgg cgactcaacc agctcaacaa cgcagccacc atcttggtct tcttcactgt ggtcatcaat gttttcatta cagccttcgg ggcacataaa acagggttcc tggctgccag ggcctcaagg aatcctctct gaatgcagcc tgggacccag gttctgggcc tggaacttct gcctccttcc tccgtgatct gccaggctcg tgggcacttt ccacagccca ggagagcttc tgaaaggaca gtatagctgc ccttgctccc tacccacagc acctgagtta aaaagtgatt tttatgttat tggtctaagg gacttccatc ttggtctgaa gtcctgagct cagacgcagg tactgccagc cataccttcc tggtagcatc tgctggacct aagtaaggca tgtctgtcta aggccaagtc tgcccggctt aaggatgctg gttctgactc taccccactg cttccttctg ctccaggcct caattttccc ttcttgtaaa atggaatcta tatctataaa ggtttcttca aatcca

SEQ ID NO 5:
CGTGGTCATTGCACGGCTGAA

SEQ ID NO 6:
CTGAACCTGAATGAGGTAGAA

SEQ ID NO 7:
mipflpmfsl llllivnpin annhydkila hsrirgrdqg pnvcalqqil gtkkkyfstc knwykksicg qkttvlyecc pgymrmegmk gcpavlpidh vygtlgivga tttqrysdas klreeiegkg sftyfapsne awdnldsdir rglesnvnve llnalhshmi nkrmltkdlk ngmiipsmyn nlglfinhyp ngvvtvncar iihgnqiatn gvvhvidrvl tqigtsiqdf ieaeddlssf raaaitsdil ealgrdghft lfaptneafe klprgvleri mgdkvaseal mkyhilntlq csesimggav fetlegntie igcdgdsitv ngikmvnkkd ivtnngvihl idqvlipdsa kqvielagkq qttftdlvaq lglasalrpd geytllapvn nafsddtlsm dqrllklilq nhilkvkvgl nelyngqile tiggkqlrvf vyrtavcien scmekgskqg rngaihifre iikpaekslh eklkqdkrfs tflslleaad lkelltqpgd wtlfvptnda fkgmtseeke ilirdknalq niilyhltpg vfigkgfepg vtnilkttqg skiflkevnd tllvnelksk esdimttngv ihvvdkllyp adtpvgndql leilnkliky iqikfvrgst fkeipvtvyk piikkytkii dgvpveitek etreeriitg peikytrist gggeteetlk kllqeevtkv tkfieggdgh lfedeeikrl lqgdtpvrkl qankkvqgsr rrlregrsq SEQ ID NO 8:
mdkfwwhaaw glclvplsla qidlnitcrf agvfhvekng rysisrteaa dlckafnstl ptmaqmekal sigfetcryg fieghvvipr ihpnsicaan ntgvyiltsn tsqydtycfn asappeedct svtdlpnafd gpititivnr dgtryvqkge yrtnpediyp snptdddvss gssserssts ggyifytfst vhpipdedsp witdstdrip atrhshgsqe gganttsgpi rtpqipewli ilasllalal ilavciavns rrrcgqkkkl vinsgngave drkpsglnge asksqemvhl vnkessetpd qfmtadetrn lqnvdmkigv -continued

SEQ ID NO 9:
CCGG-CGTGGTCATTGCACGGCTGAA-CTCGAG-

TTCAGCCGTGCAATGACCACG-TTTTTG

SEQ ID NO 10:
CCGG-CTGAACCTGAATGAGGTAGAA-CTCGAG-

TTCTACCTCATTCAGGTTCAG-TTTTTG

SEQ ID NO 11:
GUAAGGCAUGUCUGUCUAAGGCC

SEQ ID NO 12:
GGCCUUAGACAGACAUGCCUUAC

SEQ ID NO 13:
CCGGCAACAAGATGAAGAGCACCAACTCGAGTTGG-

TGCTCTTCATCTTGTTGTTTTT

SEQ ID NO 14:
UUCUCCGAACGUGUCACGUTT

SEQ ID NO 15:
ACGUGACACGUUCGGAGAATT

---

The invention claimed is:

1. A method for treating anticancer drug resistance or enhancing anticancer drug sensitivity, comprising a step of administering an effective amount of an agent for reducing the expression level of a gene encoding NINJ2 (nerve injury-induced protein 2; Ninjurin 2) protein to a subject in need thereof, wherein the agent for reducing the expression level of the gene is any one or more selected from the group consisting of an antisense nucleotide, a short interfering RNA (siRNA), a short hairpin RNA, and ribozyme, which bind complementarily to the NINJ2 gene or a portion thereof, wherein the subject has gastric cancer and has resistance to anticancer drugs comprising epirubicin, cisplatin, and 5-fluorouracil.

* * * * *